(12) United States Patent
Russell et al.

(10) Patent No.: US 6,365,634 B1
(45) Date of Patent: Apr. 2, 2002

(54) NATURALLY OCCURRING COMPOUNDS AND THEIR DERIVATIVES AS CYCLOOXYGENASE 2 AND/OR 5-LIPOXYGENASE INHIBITORS

(75) Inventors: Brett A. Russell; John D. Miller, both of Seattle, WA (US); John R. Cashman, Rancho Santa Fe, CA (US); Sirimevan A. Weerawarna, Seattle, WA (US)

(73) Assignee: C-P Technology Limited Partnership, Mill Creek, WA (US)

( * ) Notice: Subject to any disclaimer, the term of this patent is extended or adjusted under 35 U.S.C. 154(b) by 0 days.

(21) Appl. No.: 09/210,343

(22) Filed: Dec. 11, 1998

Related U.S. Application Data

(60) Provisional application No. 60/095,597, filed on Aug. 5, 1998, provisional application No. 60/075,152, filed on Feb. 19, 1998, and provisional application No. 60/069,557, filed on Dec. 12, 1997.

(51) Int. Cl.$^7$ .............................................. A61K 31/05
(52) U.S. Cl. ..................................................... 514/736
(58) Field of Search ........................................ 514/736

(56) References Cited

U.S. PATENT DOCUMENTS

| 4,412,998 A | * 11/1983 | Scherm et al. ............... 424/267 |
| 5,716,625 A | 2/1998 | Hahn et al. .................. 424/401 |

OTHER PUBLICATIONS

Hahn, Gary S., "CT–746 (Cosmoderm–7) A New Compound Class which Suppresses Neurogenic Inflammation and Sensory Irritation," Cosmoderm Technologies (Jan. 12, 1998).

Hahn, Gary S., "Strontium is a Potent and Selective Inhibitor of Sensory Irritation," Cosmoderm Technologies (1997).

* cited by examiner

*Primary Examiner*—Phyllis G. Spivack
(74) *Attorney, Agent, or Firm*—Stoel Rives LLP

(57) ABSTRACT

This invention discloses methods for treating inflammation by inhibiting the production of pro-inflammatory metabolites via the cyclooxygenase and/or lipoxygenase pathways, comprising administering 4-cumylphenol or salts or solvates thereof.

19 Claims, 22 Drawing Sheets

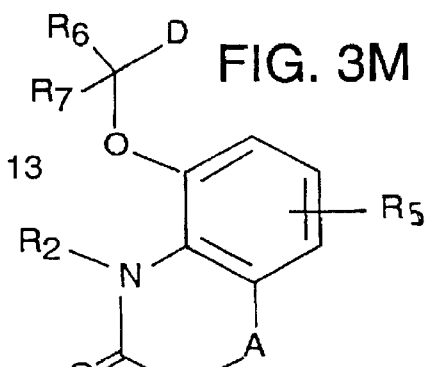
FIG. 3M
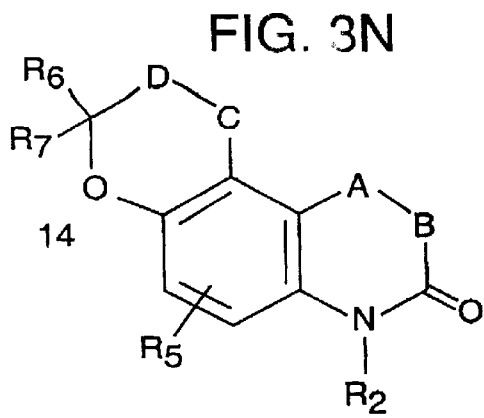
FIG. 3N
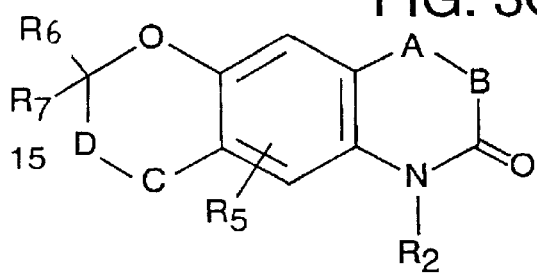
FIG. 3O
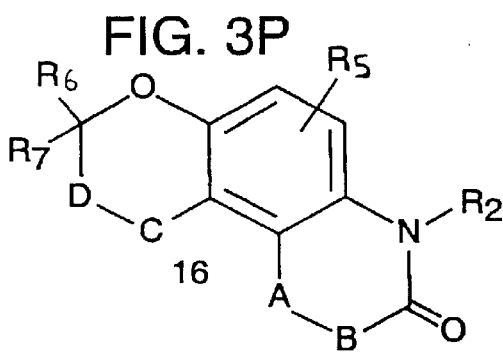
FIG. 3P
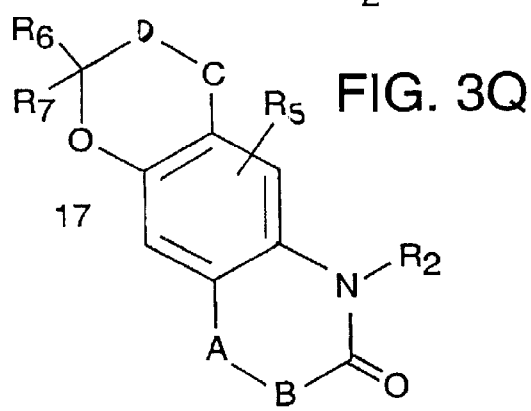
FIG. 3Q
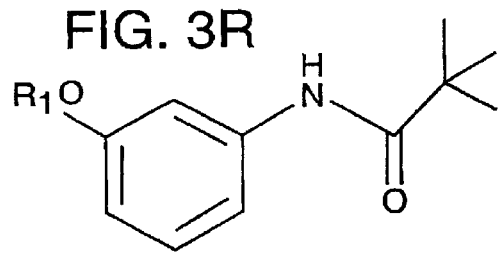
FIG. 3R
FIG. 4
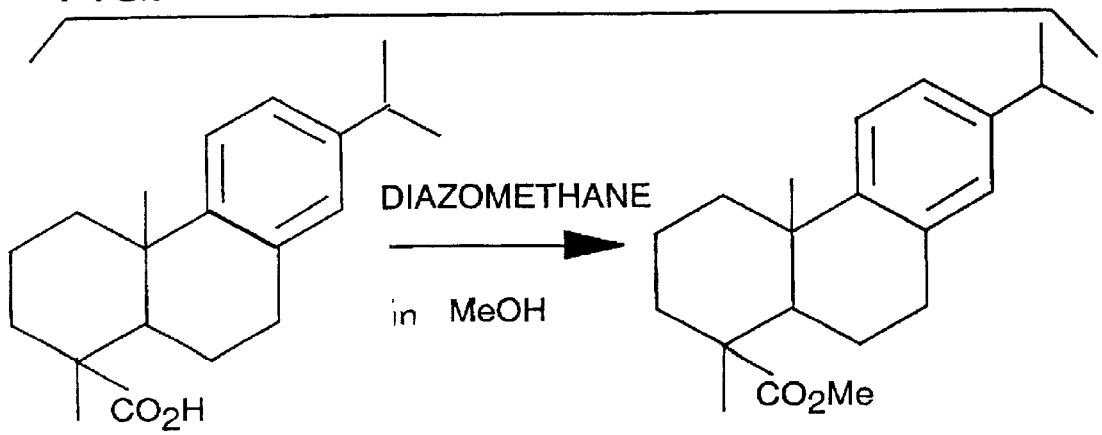

FIG. 5  NMR of Synthesized Dehydroabietic Acid Methyl Ester (DAA ME)

Inhibition of human Keratinocyte PGE2 Production by dehydroabietic acid methyl ester (DAAME).

Inhibition of human Keratinocyte LTB4 Production by dehydroabietic acid methyl ester (DAAME).

Lack of toxicity in cultures of human keratinocytes treated with dehydroabietic acid methyl ester (DAAME).

Identification of Aralkyl- and Heteroalkyl Phenols.

Inhibition of human Keratinocyte PGE2 Production by 4-Cumylphenol (4-C-P).

Lack of Toxicity in Cultures of Human Keratinocytes Treated with 4-Cumylphenol (4-C-P).

NATURALLY OCCURRING COMPOUNDS AND THEIR DERIVATIVES AS CYCLOOXYGENASE 2 AND/OR 5-LIPOXYGENASE INHIBITORS

This patent application derives priority from provisional application No. 60/069,557, filed Dec. 12, 1997, from provisional application No. 60/075,152, filed Feb. 19, 1998, and from provisional application No. 60/095,597, filed Aug. 5, 1998.

TECHNICAL FIELD

This invention relates to anti-inflammatory pharmaceutical agents and, in particular, to novel compounds isolated from a natural source for the treatment of human and animal inflammatory disorders mediated by cyclooxygenase-2 (COX II) and/or 5-lipoxygenase (5-LO).

BACKGROUND OF THE INVENTION

The process of inflammation entails a complex series of cellular and biochemical mechanisms orchestrated in such a manner so as to protect an organism from injury and pathogens. An inflammatory response is characterized by vasodialation, pain, swelling (edema), fever, the release of fluid transudate, and the infiltration of inflammatory cell types into inflamed tissues. Inflammation can be elicited by assorted types of insults and pathological states including acute injury (i.e., lacerations, abrasions), allergic reactions such as asthma, allergic rhinitis, and, allergic skin diseases, and immunological diseases such as rheumatoid arthritis, and some neurodegenerative disorders such as Alzheimer's disease.

Prostaglandins (derived from eicosanoic essential fatty acids) are produced during an inflammatory response by inflammation-related biochemical pathways and are responsible for mediating the clinical manifestations characteristic of inflammation. In addition to mediating inflammation, there is some evidence that prostaglandins are involved in mediating the proliferative capacity of some cancerous cell types (Planchon, P., Veber, N., Magnien, V., Prevost, G., Starzec, A. B., and Israel, L., (1995), Life Sciences, v57, p1233). The major source for the production of inflammation-related prostaglandins is arachidonic acid. In addition, metabolites of linoleic or eicosapentaenoic acid and other related fatty acids present in dietary constituents, or found in other sources, are potential mediators of inflammation. The prostaglandins, thromboxanes, hydroxyeicosatetraenoic acids and other metabolites derived from linoeic, eicosapentaenoic, and other fatty acids can also, in principle, participate in pro-inflammatory processes (Sinclair, H. M. (1980) "Drugs Affecting Lipid Metabolism" (Elsevien/North-Holland, Amsterdam)). Arachidonic acid (AA) can be metabolized by one of two cyclooxygenases (COX I or COX II) producing inflammatory metabolites such as prostaglandin $E_2$ ($PGE_2$), $PGI_2$, $PGF_2$-alpha, and thromboxane (TBX). The increased production of pro-inflammatory metabolites such as $PGE_2$ in inflamed tissues is due to the specific upregulation of COX II (Maier, J. A. M., Hla, T., Macaig, T. J., (1990), J. Biol. Chem., v265, p10805). The increased expression of COX II during an inflammatory response is believed to be induced (in part) by exposure to bacterial endotoxins and/or the release of pro-inflammatory cytokines (Isakson, P. C., (1995), Med. Chem. Res., v5, p344; Raz, A., Wyche, A., and Needleman, P., (1989), P.N.A.S., v86, p1657; O'Sullivan, M. G., Chilton, F. H., Huggins, E. M., McCall. E., (1992), J. Biol. Chem., v267, p14547), although other materials may increase expression of COX II as well.

In contrast, COX I is constituitively expressed in most tissues and has been proposed to be involved in the maintenance of physiological functions such as platelet aggregation, cytoprotection in the stomach, and in part, the regulation of normal kidney function (Prasit, P., Black, C. C., Chan, A. W., Ford-Hutchinson, J. Y., Gauthier, R., Gordon, D., Guay, S., Kargman, C. K., Lau, C. S., Li, J., Mancini, N., Quimet, P., Roy, P., Tagari, P., Vickers, E., Wong, R. N., Young, and R. Zamboni., (1995), Med. Chem. Res., v5, p364; Pinto, D. J., Pitts, W. J., Copeland, R. A., Covington, M. B., Trzaskos, J., Magolda, R., (1995), Med. Chem. Res., v5, p394; Whittle, B. J. R., Higgs, G. A., Eakins, K. E., Moncada, S., and Vane, J. R., (1980), Nature, v284, p271). Cloning of the human COX II gene has permitted a comparison between the two enzymes at the molecular level and has revealed a cassette of 18 amino acids near the C terminus of COX II that are absent in COX I (DeWitt, D. L., Bhattacharyya, D., Lecomte, M., and Smith, W. L., (1995), Med. Chem. Res., v5, p325). The differential expression of COX I versus COX II combined with differences at the molecular level suggests the possibility that compounds capable of binding to and inhibiting COX II, but not COX I could be developed.

In addition to the production of pro-inflammatory eicosanoid metabolites via the cyclooxygenase pathways, AA also serves as the source for the production of another class of inflammation-related metaboliotes produced by a family of related enzymes called lipoxygenases (5-, 12- or 15-LO). In particular, 5-LO catalyzes the first step of a biochemical cascade that culminates in the biosynthesis of a class of molecules termed leukotrienes (LT) such as $LTA_4$, $-B_4$, $-C_4$, and $-D_4$ (Sirois, P., Pharmacology of the Leukotrienes, Advances in Lipid Research, R. Paoletti, D. Kritchevesky, editors, Academic Press, 21: 79, 1985). Leukotrienes have been implicated as important mediators of inflammatory responses, such as anaphylaxis, suggesting that potent inhibitors of 5-LO would provide an approach to limit the deleterious effects of all the products of this pathway. Elevated 15-LO activity has been associated with conditions such as asthma and hypereosinophilia. Selective inhibition of 5-, 12-, or 15- LO may provide an agent with a definite therapeutic advantage.

Non-steroidal anti-inflammatory drugs (NSAIDS) such as aspirin are among the most frequently used drugs currently available. Originally, the medicinal utility of classical NSAIDS was suspected to be due to their ability to inhibit the activities of COX I (Mitchell, J. A., Akarasereenont, P., Thiemermann, C., Flower, R., Vane, J. R., P.N.A.S., (1993), v90, p11693; Meade, E. A., Smith, W. L., DeWitt, D. L., (1993), J. Biol. Chem., v268, p6610). Today, it is recognized that NSAIDS also have anti-inflammatory activity due to inhibition of COX II as well. Other biochemical activities associated with NSAIDS include inhibition of inflammatory mediators other than those mentioned above (i. e. histamine, serotonin, kinins), inhibition of oxidative phosphorylation, displacement of anti-inflammatory peptides from serum albumin, or displacement of peptides that hyperpolarize neuronal membranes in inflamed tissue (Foye, W. O. (1989) "Principles of Medicinal Chemistry" (Lea and Febiger/London)). However, inhibition of the constituitively expressed COX I by chronic use of NSAIDS leads to major side effects including the development of gastric ulceration and nephrotoxicity (DeWitt, D. L., Bhattacharyya, D., Lecomte, M., and Smith, W. L., (1995), Med. Chem. Res., v5, p325).

Therefore, development of an agent that selectively inhibits COX II would be useful to avoid the toxicities associated with COX I inhibition. The structure-activity relationship of potential inhibitors can be manipulated to produce such a desired selective effect. Modifications of some NSAIDS have also been made to increase therapeutic activity and decrease toxicity. For example, NSAIDS prodrugs such as sulindac have reduced toxicity, have improved half life, and have better solubility characteristics than the parent-type compound indomethacin. Prodrug inhibitors of mediators of inflammation may possess significantly improved pharmacological and pharmaceutical properties.

The key roles played by the AA metabolites produced by COX II and 5-, 12-, 15-LO in mediating inflammatory responses has prompted extensive research to identify compounds capable of specifically inhibiting the enzymatic activities of COX II, 5-, 12-, 15-LO, or more than one simultaneously (i.e., dual inhibitors). Compounds capable of inhibiting COX II (but not COX I) and/or 5-LO would be of great use as anti-inflammatory agents without the ensuing deleterious side effects common to most non-steroidal anti-inflammatory drugs. Alternatively, compounds inhibiting release of arachidonic acid or other fatty acids or compounds antagonizing proinflammatory cytokines would be of potential therapeutic use. Such inhibitory compounds would have great clinical utility in the treatment of such conditions as pain, fever, asthma, allergic rhinitis, rheumatoid arthritis, osteoarthritis, gout, adult respiratory disease syndrome, inflammatory bowel disease, endotoxic shock, ischemia-induced myocardial injury, atherosclerosis, and brain damage caused by stroke. Such inhibitors could also be used topically for the treatment of acne, sunburn, psoriasis, eczema, and related conditions.

SUMMARY OF THE INVENTION

This invention relates to a composition and method for treating inflammation by inhibiting the production of pro-inflammatory metabolites via the cyclooxygenase and/or lipoxygenase pathways. More specifically, this invention relates to the treatment of inflammation and inflammation related disorders through the use of compounds (and derivatives thereof) identified from a natural source.

Numerous compounds with anti-inflammatory activity have been chemically synthesized (T. Y. Shen, *J. Med. Chem.*, 24 1, 1981) but very few anti-inflammatory agents have been isolated from various natural product sources. Although an agent such as indomethacin can trace its route of development from observations concerning abnormal human indole metabolism, the vast number of salicylic, anilino, anthranilic acid, benzothiozines, and gold compounds find their origins from synthetic medicinal chemistry. In contrast, fewer anti-inflammation agents have been discovered from natural product searches. The source, from which compounds of the invention were identified, is a natural peat bog located in south-central Washington state containing compounds derived from plant, animal, marine, and microbial sources. In addition, the peat bog environment is conducive to microbial processing of compounds originating from plant and animal sources producing a highly variable and heterogeneous mixture of potentially biologically active molecules.

Additional objects and advantages of this invention will be apparent from the following detailed description of preferred embodiments thereof which proceeds with reference to the accompanying drawings.

BRIEF DESCRIPTION OF THE DRAWINGS

FIG. 4 is a reaction diagram showing the synthesis of dehydroabietic acid methyl ester (DAAME).

DETAILED DESCRIPTION OF PREFERRED EMBODIMENTS

Section I)

Figure 1:
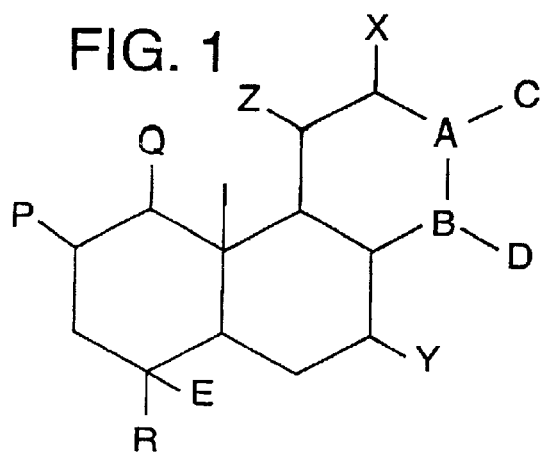
FIG. 1 is a structural formula showing rigid analogs of arylbutyric acid esters.

Section I describes rigid analogs of aryl butyric acid esters represented by formula I presented in FIG. 1 and the pharmaceutically acceptable salts thereof, wherein A and B constitute part of a 5- or 6- member ring system from aromatic or partially unsaturated or unsaturated heterocyclic and carbocyclic rings wherein A and/or B is optionally substituted with hydrido, acyl, halo, lower acyl, lower haloalkyl, oxo, cyano, nitro, carboxyl, amino, lower alkoxy, amino carbonyl, lower alkoxycarbonyl, alkyl amino, aryl amino, lower carboxyalkyl, lower cyanoalkyl, lower hydroxyalkyl, alkylthio, alkyl sulfinyl and aryl, lower aralkylthio, lower alkylsulfinyl, lower alkylsulfonyl, aminosulfonyl, lower N-arylaminosulfonyl, lower arylsulfonyl, lower N-alkyl-N-arylaminosulfonyl; wherein aryl is selected from phenyl, biphenyl, and naphthyl, and 5- and 6-membered heteroaryl, wherein aryl is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, and lower carbonylalkoxy; wherein the carboxylic group is optionally substituted with a substituent selected from hydrido, alkyl, halo, and alkoxy.

A preferred class of compounds includes compounds of formula I wherein the A, B ring system is a radical selected from thienyl, oxazolyl, furyl, pyrolyl, thiazolyl, imidazolyl, isthiazolyl, isoxazoly, pyrazolyl, cyclopentyl, phenyl, and pyridyl;

wherein X and Z are selected from hydrido, acyl, halo, lower acyl, lower haloalkyl, oxo, cyano, nitro, carboxyl, amino, lower alkoxy, amino carbonyl, lower alkoxycarbonyl, alkyl amino, aryl amino, lower carboxyalkyl, lower cyanoalkyl, lower hydroxyalkyl, alkylthio, alkyl sulfinyl and aryl, lower aralkylthio, lower alkylsulfinyl, lower alkylsulfonyl, aminosulfonyl, lower N-arylaminosulfonyl, lower arylsulfonyl, lower N-alkyl-N-arylaminosulfonyl; wherein Ar is selected from phenyl, biphenyl, and naphthyl, and 5- and 6-membered heteroaryl, wherein Ar is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, and lower carbonylalkoxy;

wherein P, Q, and Y are selected from hydrido, acyl, halo, lower alkyl, lower haloalkyl, oxo, cyano, nitro, carboxyl, amino, lower alkoxy, amino carbonyl, lower alkoxycarbonyl, alkyl amino, aryl amino, lower carboxyalkyl, lower cyanoalkyl, lower hydroxyalkyl, alkylthio, alkyl sulfinyl and aryl, lower aralkylthio, lower alkylsulfinyl, lower alkylsulfonyl, aminosulfonyl, lower N-arylaminosulfonyl, lower arylsulfonyl, lower N-alkyl-N-arylaminosulfonyl;

wherein Ar is selected from phenyl, biphenyl, and naphthyl, and 5- and 6-membered heteroaryl, wherein A.r is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, and lower carbonylalkoxy;

wherein R is selected from hydrido, acyl, halo, lower alkyl, lower haloalkyl, oxo, cyano, nitro, carboxyl, amino, lower alkoxy, amino carbonyl, lower alkoxycarbonyl, alkyl amino, aryl amino, lower carboxyalkyl, lower cyanoalkyl, lower hydroxyalkyl, alkylthio, alkyl sulfinyl and aryl, lower aralkylthio, lower alkylsulfinyl, lower alkylsulfonyl, aminosulfonyl, lower N-arylaminosulfonyl, lower arylsulfonyl, lower N-alkyl-N-arylaminosulfonyl; wherein Ar is selected from phenyl, biphenyl, and naphthyl, and 5- and 6-membered heteroaryl, wherein Ar is optionally substituted with one or two substituents selected from halo, hydroxyl, amino, nitro, cyano, carbamoyl, lower alkyl, lower alkenyloxy, lower alkoxy, lower alkylthio, lower alkylsulfinyl, lower alkylsulfonyl, lower alkylamino, lower dialkylamino, lower haloalkyl, lower alkoxycarbonyl, lower N-alkylcarbamoyl, lower N,N-dialkylcarbamoyl, lower alkanoylamino, lower cyanoalkoxy, lower carbamoylalkoxy, lower carbonylalkoxy; wherein E is selected from lower alkyl, lower alkenyl, lower alkynyl, lower alkyloxy, lower hydroalkyloxy, lower hydroalkyoxyalkyl, lower oximinoalkoxy, lower oximinoalkyloxyalkyl, lower carbonylalkyloxy, lower (alkyl)oximinoalkoxy, lower (alkyl)oximinoalkoxyalkyl, lower carbonylalkyloxyalkyl, lower hydroxyalkylthio, lower hydroxyalkylthioalkyl, lower (alkyl)oximinoalkylthio, lower (alkyl)oximinoalkylthio, lower carbonylalkylthio, lower carbonylalkylthioalkyl, lower alkylthio, lower alkylcarbonyl, lower cycloalkyl, phenyl, lower haloalkyl, 5- or 6-membered heterocyclo, lower cycloalkyl, lower aralkyl, lower heterocycloalkyl, lower aklynylthio, lower alkenyloxy, lower alkynyloxy, lower alkenoxyalkyl, lower alkynyloxyalkyl, phenylcarbonyl, lower aralkylcarbonyl, lower alkylaminocarbonylalkyl, lower N-alkylaminocarbonyl, N-phenylaminocarbonyl, lower N,N-dialkylaminocarbonyl, lower N-alkyl-N-arylaminocarbonyl, lower heterocycloaminocarbonyl, and lower alkylcarbonylalkyl.

The term "hydrido" denotes a single hydrogen atom (H). When used, either alone or in conjunction within other terms such as "haloalkyl", "sulfonyl", etc., the term "alkyl" embraces linear or branched radicals having one to about twenty carbon atoms. Examples of such radicals include methyl, ethyl n-propyl, isopropyl, n-butyl, tert-butyl, sec-butyl, pentyl, and the like. The term "alkenyl" embraces linear or branched radicals, having at least one carbon to carbon double bond, of two to about twenty carbon atoms. The term "lower alkynyl" embraces radicals having two to about twenty carbon atoms. The terms "alkenyl" embrace radicals having cis and trans orientations, or alternatively, "E" and "Z" orientations.

Preferred cycloalkyl radicals include cyclopropyl, cyclobutyl, cyclopentyl, and cyclohexyl. The term "cycloalkenyl" includes partially unsaturated carbocyclic radicals having three to twelve carbon atoms. The term "halo" means halogens such as fluorine, chlorine, bromine, or iodine. The term "haloalkyl" means one or more alkyl carbon atoms is substituted with a halogen atom. "Lower haloalkyl" means radicals having one to ten carbon atoms. The term "hydroxyalkyl" means linear or branched alkyl radicals substituted with one or more hydroxyl radicals. The term "alkoxy" and "alkyloxy" embraces linear or branched oxygen-containing radicals having alkyl moieties of between one and twenty carbon atoms.

The term "hydroxyalkyl" includes linear or branched alkyl radicals having one to about twenty carbon atoms any one of which may be substituted with a hydroxyl group.

The term cyanoalkyl includes linear or branched alkyl radicals having one to about twenty carbon atoms any one of which could be substituted with one or more cyano groups.

The term alkoxyalkyl includes alkyl groups having one or more alkoxy radicals attached to the alkyl group. The alkoxy radical may be further substituted with one or more halo atoms. Preferred haloalkoxy groups may one to twenty carbons.

The term alkenyloxy includes radicals having alkenyl moieties of two to twenty carbon atoms attached to an oxygen atom. Alkenyloxy radicals having two to twenty carbon atoms attached to an oxygen atom may be substituted with one or more alkenyl groups.

The term "aryl" includes, but is not limited to, a carboxylic aromatic ring system having one, two, or three rings attached together in a pendent arrangement or as a fused system. The term "aryl" includes phenyl, naphthyl, tetrahydronaphthyl, indone, biphenyl, and aryl moieties described above with substituents.

The term "heterocyclo" includes saturated, partially unsaturated, and unsaturated heteroatoms containing 3 to 6 membered cyclic systems where heteroatoms are selected from oxygen, nitrogen, sulfur, and phosphorous.

The term "heteroaryl" includes unsaturated heterocyclo radicals containing three to six membered heteromonocyclic groups where the heteroatoms are selected from oxygen, nitrogen, sulfur, and phosphorous. The term also includes radicals where heterocyclo groups are fused with aryl groups.

The term "alkylthio" includes radicals containing linear or branched alkyl groups of one to about twenty carbon atoms attached to a divalent sulfur atom.

The term "alkylthioalkyl" includes an alkylthio group attached to a alkyl radical of about one to twenty carbon atoms through a divalent sulfur atom.

The term "oximinoalkoxy" includes alkoxy radicals having one to about twenty carbon atoms, any one of which may be substituted with an oximino radical.

The term "alkenylthio" includes groups containing a linear or branched alkenyl radical of two to about twenty carbon atoms attached to a divalent sulfur atom.

The term "alkynylthio" includes radicals containing a linear or branched alkynyl radical from two to about twenty carbon atoms attached to a divalent sulfur atom with an alkynyl moiety attached to on or more of the carbon atoms.

The term "alkylsulfinyl" includes a radical containing a linear or branched alkyl group of one to about twenty carbon atoms, attached to a sulfinyl group.

The term "sulfonyl" includes a —SO$_2$— group attached to an alkyl of one to about twenty carbon atoms.

The term "sulfamyl", "aminosulfonyl", and "sulfonamidyl" include the —SO$_2$NH$_2$ radical attached to various alkyl or aryl functionalities.

The term "aroyl" includes aryl radicals with a carbonyl group.

The term "aminoalkyl" includes alkyl radicals from one to about twenty carbon atoms that are substituted with amino groups.

The term "arylamino" includes amino groups substituted with one or more aryl radicals.

The term "alkylamino" includes amino groups substituted with one or more alkyl groups with one to about twenty carbon atoms.

When the above radicals are incorporated into the parent molecule, the present invention includes all possible stereochemical arrangements of the substituents. In addition, the optional agent includes racemic or stereochemically pure compounds.

Section II)

Figure 2:
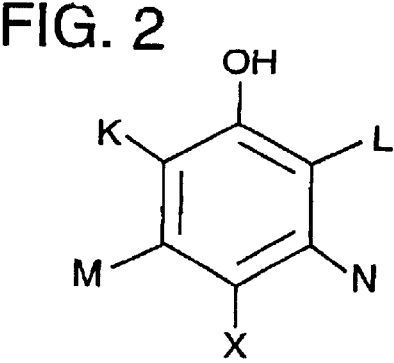
FIG. 2 is a structural formula showing aralkyl or heteroaralkyl phenols.
Figure 2A:
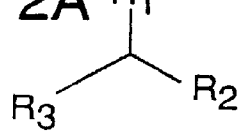
FIG. 2A is a partial structural formula showing a trisubstituted carbon that may be utilized in up to three of the groups K, L, M, N, or X in the structural formula of FIG. 2.

Section II describes "aralkyl" or "heteroaralkyl" phenols of the formula presented in FIG. 2 or pharmaceutically acceptable salts or solvates thereof wherein:

(A) of the K, L, M, N and X; one, two, or three groups are optionally assigned as the trisubstituted carbon as in the partial structure shown in FIG. 2A;

(1) wherein $R_1$ is selected from;

(i) "aryl" selected from phenyl, biphenyl, and naphthyl optionally having one or two ring hydrogens substituted with substituents selected from Cl, Br, I, —OR$_4$, —R$_5$, —OC(O)R$_6$, —C(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$, and —S(O)$_2$NR$_{16}$R$_{17}$;

(ii) "heteroaryl" (means heterocyclic aromatic) i.e. cyclic groups having at least one oxygen, sulfur, or nitrogen heteroatom interrupting a carbocyclic ring structure and having a sufficient number of delocalized pi electrons to provide aromatic character, said rings preferably containing from 2 to 14 carbon atoms, e.g, 2-, 3-, and 4-pyridyl, 2- and 3-furyl, 2- and 3-thienyl, 2-, 4-, and 5-thiazolyl, 2-, 4-, and 5-imidazolyl, 2-, 4-, and 5-pyrimidinyl, 2-pyrazinyl, 3- and 4-pyridazinyl, 3-, 5-, and 6-[1,2,4-triazinyl], 3- and 5-[1,2,4-thia-dizolyl], 2-, 3-, 4-, 5-, 6-, and 7-benzofuranyl, 2-, 3-, 4-, 5-, 6-, and 7-indolyl, 3-, 4-, and 5-pyrazolyl, 2-, 4-, and 5-oxazolyl etc., optionally having one or two ring hydrogens substituted with substituents selected from Cl, Br, I, —OR$_4$, —R$_5$, —OC(O)R$_6$, —OC(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$, and —S(O)$_2$NR$_{16}$R$_{17}$;

(2) wherein $R_2$ and $R_3$ are the same or different and are selected from;

(i) branched or unbranched alkyl of one to eight carbon atoms;

(ii) cycloalkyl ring (means saturated carbocyclic ring) having from 3 to 8 atoms;

(iii) cycloalkenyl ring (cycloalkenyl means carbocyclic ring having from 3 to 8 carbon atoms and at least one carbon to carbon double bond in the ring);

(iv) heterocyclic ring containing 2 to 6 carbon atoms, which may optionally contain at least one carbon to carbon double bond and which contains at least one heteroatom selected from nitrogen, oxygen, or sulfur; representative heterocycles include, but are not limited to: pyrrolidine, piperidine, piperazine, heptamethyleneimine, hexamethyleneimine, homopiperazine, perhydroindole, azetidine, 4-piperidinopiperidine, 1-azacycloheptane, perhydroisoquioline, decahydroquinoline, 1-phenylpiperazine, 4-phenylpiperidine, 1-(fluorophenyl)piperazine, 1,3,5-hexahydrotriazine, morpholine, phenylmorpholine, thiomorphline, tetrahydrothiophene, thiazolidine, ω-thiocaprolactam, 1,4-thioxane, 1,3-dithiane, 1,4,7-trithiacyclononane, 1,3,5-trithiane, tetrahydrofuran, tetramethyleneoxide, tetrahydropyran, 1,3,5-trioxane, oxepane, and the like, optionally having one or two ring hydrogens substituted with substituents selected from Cl, Br, I, —OR$_4$, —R$_5$, —OC(O)R$_6$, OC(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$, and —S(O)$_2$NR$_{16}$R$_{17}$;

(v) substituted alkyl wherein the alkyl chain is from one to three carbon atoms and the substituent is selected from "aryl" selected from phenyl, biphenyl and naphthyl optionally having one or two ring hydrogens substituted with substituents selected from Cl, Br, I, —OR$_4$, —R$_5$, —OC(O)R$_6$, —OC(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$, and —S(O)$_2$NR$_{16}$R$_{17}$;

(vi) substituted alkyl wherein the alkyl chain is from one to three carbon atoms and the substituent is selected from "heteroaryl" (means heterocyclic aromatic) i.e. cyclic groups having at least one oxygen, sulfur, or nitrogen heteroatom interrupting a carbocyclic ring structure and having a sufficient number of delocalized pi electrons to provide aromatic character, said rings preferably containing from 2 to 14 carbon atoms, e.g, 2-, 3-, and 4-pyridyl, 2- and 3-furyl, 2- and 3-thienyl, 2-, 4and 5-thiazolyl, 2-, 4-, and 5-imidazolyl, 2-, 4-, and 5-pyrimidinyl, 2-pyrazinyl, 3- and 4-pyridazinyl, 3-, 5-, and 6-[1,2,4-triazinyl], 3- and 5-[1,2,4-thia-diazolyl], 2-, 3-, 4-, 5-, 6-, and 7-benzofuranyl, 2-, 3-, 4-, 5-, 6-, and 7-indolyl, 3-, 4-, 5-pyrazolyl, 2-, 4-, and 5-oxazolyl etc., optionally having one or two ring hydrogens substituted with substituents selected from Cl, Br, I, —OR$_4$, —R$_5$, —OC(O)R$_6$, OC(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$ and —S(O)$_2$NR$_{16}$R$_{17}$;

(3) R$_1$ and R$_2$ are methylene, methine, or quarternary carbons of:
  (i) cycloalkyl ring (means saturated carbocyclic ring) having from 3 to 8 atoms;
  (ii) cycloalkenyl ring (cycloalkenyl means carbocyclic ring having from 3 to 8 carbon atoms and at least one carbon to carbon double bond in the ring);
  (iii) heterocyclic ring containing 2 to 6 carbon atoms, which may optionally contain at least one carbon-carbon double bond and which contains at least one heteroatom selected from nitrogen, oxygen, or sulfur; representative heterocycles include, but are not limited to: pyrrolidine, piperidine, piperazine, heptamethyleneimine, hexamethyleneimine, homopiperazine, perhydroindole, azetidine, 4-piperidinopiperidine, 1-azacycloheptane, perhydroisoquioline, decahydroquinoline, 1-phenylpiperazine, 4-phenylpiperidine, 1-(fluorophenyl)piperazine, 1,3,5-hexahydrotriazine, morpholine, phenylmorpholine, thiomorphline, tetrahydrothiophene, thiazolidine, ω-thiocaprolactam, 1,4-thioxane, 1,3-dithiane, 1,4,7-trithiacyclononane, 1,3,5-trithiane, tetrahydrofuran, tetramethyleneoxide, tetrahydropyran, 1,3,5-trioxane, oxepane and the like, optionally having one or two ring hydrogens substituted with substituents selected from Cl, Br, I, —OR$_4$, —R$_5$, —OC(O)R$_6$, OC(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$, and —S(O)$_2$NR$_{16}$R$_{17}$;

(B) of the K, L, M, N, and X not assigned as above are selected:
  (1) wherein K, L, M, N, and X are the same or different and are selected from;
    (i) H, Cl, Br, I, —OR$_4$, —R$_5$, —OC(O)R$_6$, OC(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$, and —S(O)$_2$NR$_{16}$R$_{17}$;
    (ii) "aryl" selected from phenyl, biphenyl, and naphthyl optionally having one or two ring hydrogens substituted with substituents selected from Cl, Br, I, —OR$_4$, —R$_5$, —OC(O)R$_6$, —OC(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$, and —S(O)$_2$NR$_{16}$R$_{17}$;
    (iii) "heteroaryl" (means heterocyclic aromatic) i.e. cyclic groups having at least one O, S, N heteroatom interrupting a carbocyclic ring structure and having a sufficient number of delocalized pi electrons to provide aromatic character, said rings preferably containing from 2 to 14 carbon atoms, e.g., 2-, 3- and 4-pyridyl, 2- and 3-furyl, 2- and 3-thienyl, 2-, 4-, and 5-thiazolyl, 2-, 4-, and 5-imidazolyl 2-, 4- and 5-pyrimidinyl, 2-pyrazinyl, 3- and 4-pyridazinyl, 3-, 5-, and 6-[1,2,4-triazinyl], 3- and 5-[1,2,4-thiadizolyl], 2-, 3-, 4-, 5-, 6-, and 7-benzofuranyl, 2-, 3-, 4-, 5-, 6-, and 7- indolyl, 3-, 4-, and 5-pyrazolyl, 2-, 4-, and 5-oxazolyl etc., optionally having one or two ring hydrogens substituted with substituents selected from Cl, Br, I, —OR$_4$, —R$_5$, —OC(O)R$_6$, -OC(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$, and —S(O)$_2$NR$_{16}$R$_{17}$;

(C) Certain compounds of this invention may exist in isomeric forms. The invention contemplates all such isomers both in pure form and admixture, including racemic mixtures.

(D) Certain compounds of the invention with carboxylic acid functional group or phenolic hydroxyl group may form pharmaceutically acceptable metal and amine salts. Examples of such metal salts are the sodium, potassium, calcium, aluminum, gold, and silver salts. Examples of such amine salts are formed with pharmaceutically acceptable amines such as ammonia, hydroxyalkylamines, N-methylgiucamine, and the like. All such salts and free carboxylic acids and phenolic compounds are contemplated in this invention.

(E) Certain compounds of the invention e.g., those with a basic primary, secondary, or tertiary amine functional group, also form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, and other suitable mineral and carboxylic acids. Amine salts and free base forms of amines are contemplated in this invention.

(F) Certain compounds of this invention may exist in unsolvated as well as solvated forms, including hydrated forms. This invention contemplates both unsolvated forms and solvated forms, with pharmaceutically acceptable solvents such as water, ethanol, and the like.

(G) One most preferred compound of this invention is represented by the formula presented in FIG. 3;

(H) "aralkyl" means alkyl group, in which one of the hydrogen atoms is substituted with an "aryl" selected from phenyl, biphenyl, and naphthyl optionally having one or two ring hydrogens substituted with substituents selected from Cl, Br, I, —OR$_4$, —R$_5$, —OC(O)R$_6$, —OC(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$, and —S(O)$_2$NR$_{16}$R$_{17}$;

(I) "Heteroaralkyl" means alkyl group in which one of the hydrogen atoms is substituted with a "heteroaryl" (means heterocyclic aromatic) i.e. cyclic groups having at least one O, S, N heteroatom interrupting a carbocyclic ring structure and having a sufficient number of delocalized pi electrons to provide aromatic character, said rings preferably containing from 2 to 14 carbon atoms, e.g, 2-, 3- and 4-pyridyl, 2- and 3-furyl, 2- and 3-thienyl, 2-, 4-, and 5-thiazolyl, 2-, 4-, and 5-imidazolyl, 2-, 4- and 5-pyrimidinyl, 2-pyrazinyl, 3- and 4-pyridazinyl, 3-, 5- and 6-[1,2,4-triazinyl], 3- and 5-[1,2,4-thiadiazolyl], 2-, 3-, 4-, 5-, 6-, and 7-benzofuranyl, 2-, 3-, 4-, 5-, 6-, and 7-indolyl, 3-, 4-, and 5-pyrazolyl, 2-, 4-, and 5-oxazolyl etc., optionally having one or two ring hydrogens substituted with substituents selected from Cl, Br, I, —OR$_4$, —R$_5$, —OC(O)R$_6$, -OC(O)NR$_7$R$_8$, —C(O)R$_9$, —CN, —NR$_{10}$R$_{11}$, —SR$_{12}$, —S(O)R$_{13}$, —S(O)$_2$R$_{14}$, —C(O)OR$_{15}$, and —S(O)$_2$NR$_{16}$R$_{17}$;

(J) C) R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, and R$_{17}$ are the same or different and are branched or unbranched alkyl groups from one to eight carbon atoms or hydrogen radicals.

The compounds presented in sections I and II above can be useful for, but not limited to, the treatment of inflammation related disorders, such as an analgesic in the treatment of pain and headaches, or as an antipyretic for the treatment of a fever. For example, such compounds can be useful to treat various forms of arthritis, asthma, bronchitis, cancer, menstrual cramps, tendinitis, bursitis, psoriasis, eczema, burns, and dermatitis. In addition, such compounds can also be useful to treat inflammation in diseases such as vascular diseases, migraine headaches, periarteritis nodosa, thyroiditis, aplastic anemia, Hodgkin's disease, sclerodoma, rheumatic fever, type I diabetes, sarciodosis, mayasthenia gravis, gingivitis, polymyositis, nephrotic syndrome, hypersensitivity, and swelling occurring after injury, and the like. These compounds can also be useful to treat neurodegenerative diseases associated with inflammation such as Alzheimer's disease, Parkinson's disease, and multiple sclerosis. As a dual COX II/5-lipoxygenase inhibitor, the compounds detailed in section I (rigid analogs of aryl butyric acid esters) can be useful for the treatment of endotoxic shock syndrome, allergic rhinitis, respiratory distress syndrome, atherosclerosis, and central nervous system damage caused by stroke.

Section III)

Figure 3A:
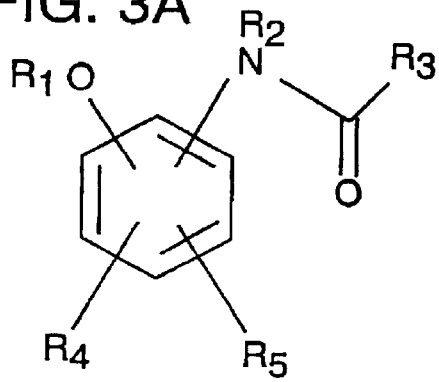
FIG. 3A is a structural formula showing anilinamide phenolic ether compounds.
Figure 3B:
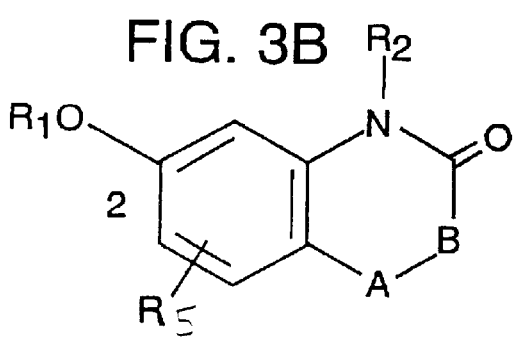
FIGS. 3B–3Q are structural formulas showing additional examples of anilinamide phenolic ether compounds.
Figure 3C:
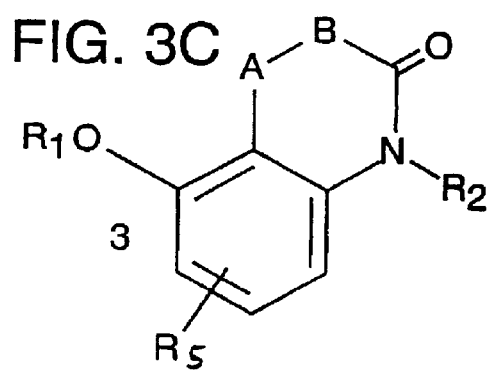
FIG. 3R is a structural formula showing a preferred example of an anilinamide phenolic ether compound.
Figure 3D:
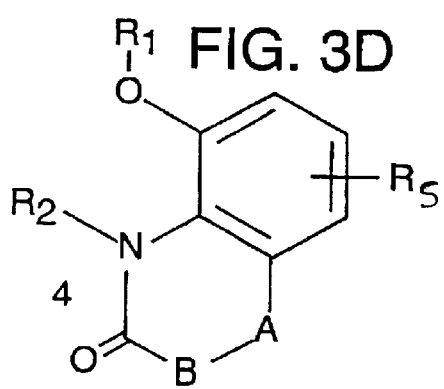
Figure 3E:
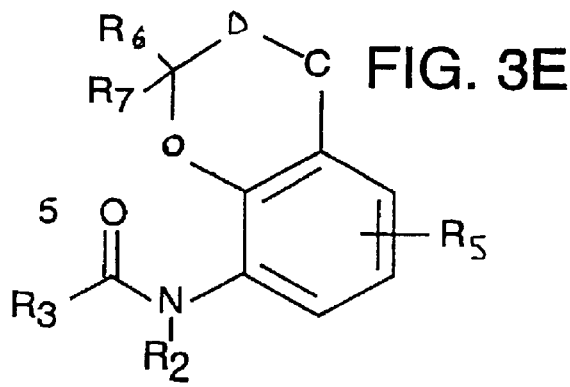
Figure 3F:
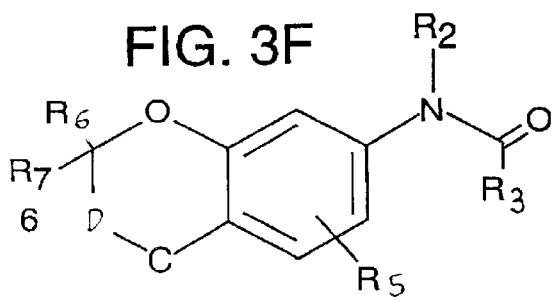
Figure 3G:
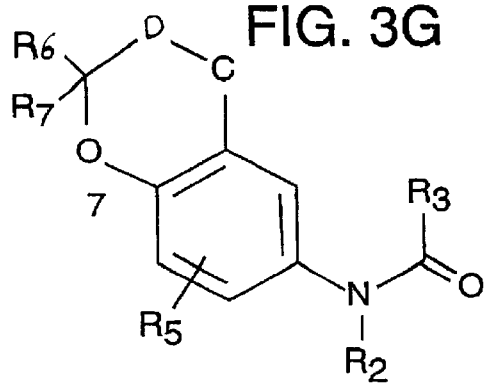
Figure 3H:
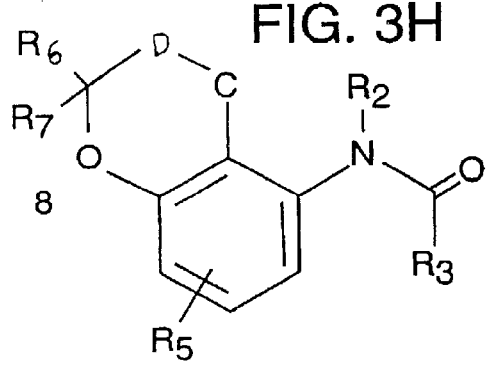
Figure 3I:
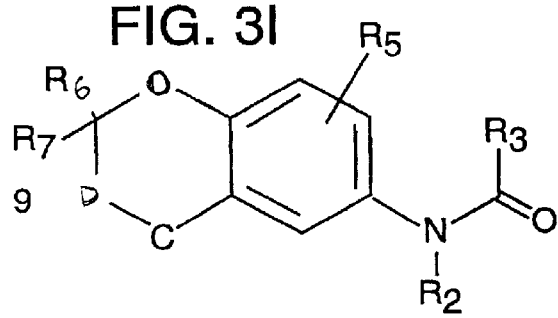
Figure 3J:
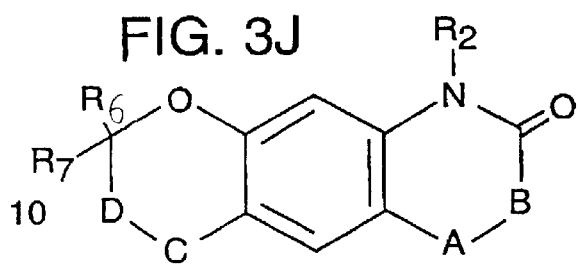
Figure 3K:
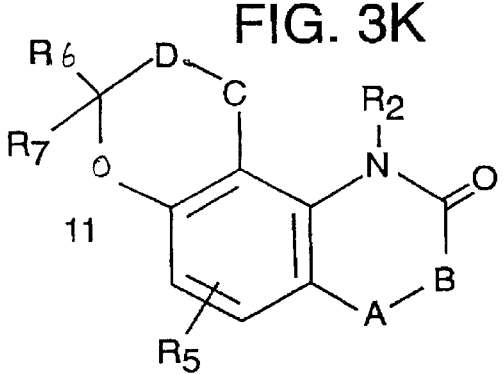
Figure 3L:
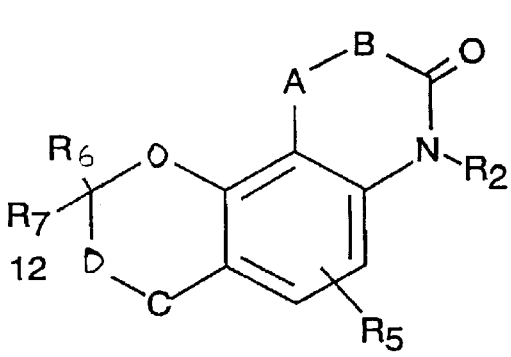

Section III describes anilinamide phenolic ether compounds represented by the formula in FIG. 3A and by the example structural formulas presented in FIGS. 3B–3Q or pharmaceutically acceptable salts or solvates thereof (1) wherein R$_1$, R$_2$, R$_3$, R$_4$, R$_5$, R$_6$, and R$_7$ are optionally selected from;

(i) "aryl" selected from phenyl, biphenyl and naphthyl optionally having one or two ring hydrogens substituted with substituents selected from Cl, Br, I, —OR$_8$, —R$_9$, —OC(O)R$_{10}$, —OC(O)NR$_{11}$R$_{12}$, —C(O)R$_{13}$, —CN, -NR$_{14}$R$_{15}$, —SR$_{16}$, -S(O)R$_{17}$, —S(O)$_2$R$_{18}$, —C(O)OR$_{19}$, and —S(O)$_2$NR$_{20}$R$_{21}$;

(ii) "heteroaryl" (means heterocyclic aromatic) i.e. cyclic groups having at least one oxygen, sulfur, or nitrogen heteroatom interrupting a carbocyclic ring structure and having a sufficient number of delocalized pi electrons to provide aromatic character, said rings preferably containing from 2 to 14 carbon atoms, e.g, 2-, 3- and 4-pyridyl, 2- and 3-furyl, 2- and 3-thienyl, 2-, 4-, and 5-thiazolyl, 2-, 4-, and 5-imidazolyl, 2-, 4-, and 5-pyrimidinyl, 2-pyrazinyl, 3- and 4-pyridazinyl, 3-, 5- and 6-[1,2,4-triazinyl], 3- and 5-[1,2,4-thia-dizolyl], 2-, 3-, 4-, 5-, 6-, and 7-benzofuranyl, 2-, 3-, 4-, 5-, 6-, and 7-indolyl, 3-, 4-, and 5-pyrazolyl, 2-, 4-, and 5-oxazolyl etc., optionally having one or two ring hydrogens substituted with substituents selected from Cl, Br, I, —OR$_8$, —R$_9$, —OC(O)R$_{10}$, OC(O)NR$_{11}$R$_{12}$, —C(O)R$_{13}$, —CN, —NR$_{14}$R$_{15}$, —SR$_{16}$, —S(O)R$_{17}$, —S(O)$_2$R$_{18}$, —C(O)OR$_{19}$, and —S(O)$_2$NR$_{20}$R$_{21}$;

(iii) branched or unbranched alkyl chain of one to five carbon atoms;

(iv) substituted alkyl wherein the alkyl chain is from one to three carbon atoms and the substituent is selected from "aryl" selected from phenyl, biphenyl, and naphthyl optionally having one or two ring hydrogens substituted with substituents selected from Cl, Br, I, —OR$_8$, —R$_9$, —OC(O)R$_{10}$, —OC(O)NR$_{11}$R$_{12}$, —C(O)R$_{13}$, —CN, —NR$_{14}$R$_{15}$, —SR$_{16}$, —S(O)R$_{17}$, —S(O)$_2$R$_{18}$, —C(O)OR$_{19}$, and —S(O)$_2$NR$_{20}$R$_{21}$;

(v) substituted alkyl wherein the alkyl chain is from one to three carbon atoms and the substituent is selected from "heteroaryl" (means heterocyclic aromatic) i.e. cyclic groups having at least one oxygen, sulfur, or nitrogen heteroatom interrupting a carbocyclic ring structure and having a sufficient number of delocalized pi electrons to provide aromatic character, said rings preferably containing from 2 to 14 carbon atoms, e.g, 2-, 3- and 4-pyridyl, 2- and 3-furyl, 2- and 3-thienyl, 2-, 4-, and 5-thiazolyl, 2-, 4-, and 5-imidazolyl, 2-, 4-, and 5-pyrimidinyl, 2-pyrazinyl, 3- and 4-pyridazinyl, 3-, 5-, and 6-[1,2,4-triazinyl], 3- and 5-[1,2,4-thia-dizolyl], 2-, 3-, 4-, 5-, 6-, and 7-benzofuranyl, 2-, 3-, 4-, 5-, 6-, and 7-indolyl, 3-, 4-, and 5-pyrazolyl, 2-, 4-, and 5-oxazolyl etc., optionally having on —OC(O)R$_{10}$, —OC(O)NR$_{11}$R$_{12}$, —C(O)R$_{13}$, —CN, —NR$_{14}$R$_{15}$, —SR$_{16}$, —S(O)R$_{17}$, —S(O)$_2$R$_{18}$, —C(O)OR$_{19}$, and —S(O)$_2$NR$_{20}$R$_{21}$;

(2) The substituents R$_1$, R$_2$, R$_4$, R$_5$, R$_6$, and R$_7$ may also be optionally selected as hydrogen;

(3) The substituents R$_4$ and R$_5$ may be optionally substituted as Cl, Br, I, —OR$_8$, —R$_9$, —OC(O)R$_{10}$, —OC(O)NR$_{11}$R$_{12}$, —C(O)R$_{13}$, —CN, —NR$_{14}$R$_{15}$, —SR$_{16}$, —S(O)R$_{17}$, —S(O)$_2$R$_{18}$, —C(O)OR$_{19}$, and —S(O)$_2$NR$_{20}$R$_{21}$;

(4) The ring substituents A, B, C, and D are optionally selected from CH$_2$, O, S, NH;

(5) R$_8$, R$_9$, R$_6$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, and R$_{21}$are the same or different and are branched or unbranched alkyl groups from one to eight carbon atoms.

(6) The most preferred formula is shown in FIG. 3R.

(C) Certain compounds of this invention may exist in isomeric forms. The invention contemplates all such isomers both in pure form and admixture, including racemic mixtures.

(D) Certain compounds of the invention with carboxylic acid functional group or phenolic hydroxyl group may form pharmaceutically acceptable metal and amine salts.

Examples of such metal salts are the sodium, potassium, calcium, aluminum, gold, and silver salts. Examples of such amine salts are formed with pharmaceutically acceptable amines such as ammonia, hydroxyalkylamines, N-methylglucamine, and the like. All such salts and free carboxylic acids and phenolic compounds are contemplated in this invention.

(E) Certain compounds of the invention e.g., those with a basic primary, secondary or tertiary amine functional group, also form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic, and other suitable mineral and carboxylic acids. Amine salts and free base forms of amines are contemplated in this invention.

(F) Certain compounds of this invention may exist in unsolvated as well as solvated forms, including hydrated forms. This invention contemplates both unsolvated forms and solvated forms, with pharmaceutically acceptable solvents such as water, ethanol, and the like.

EXAMPLE 1
General Synthetic Procedures

The compound described in section I (rigid analogs of aryl butyric acid esters) can be synthesized following the general procedure described in FIG. 4. The compound described section II (4-cumylphenol) can be obtained from commercial sources.

1A: Synthesis of Dehydroabietic Acid Methyl Ester

Figure 5:
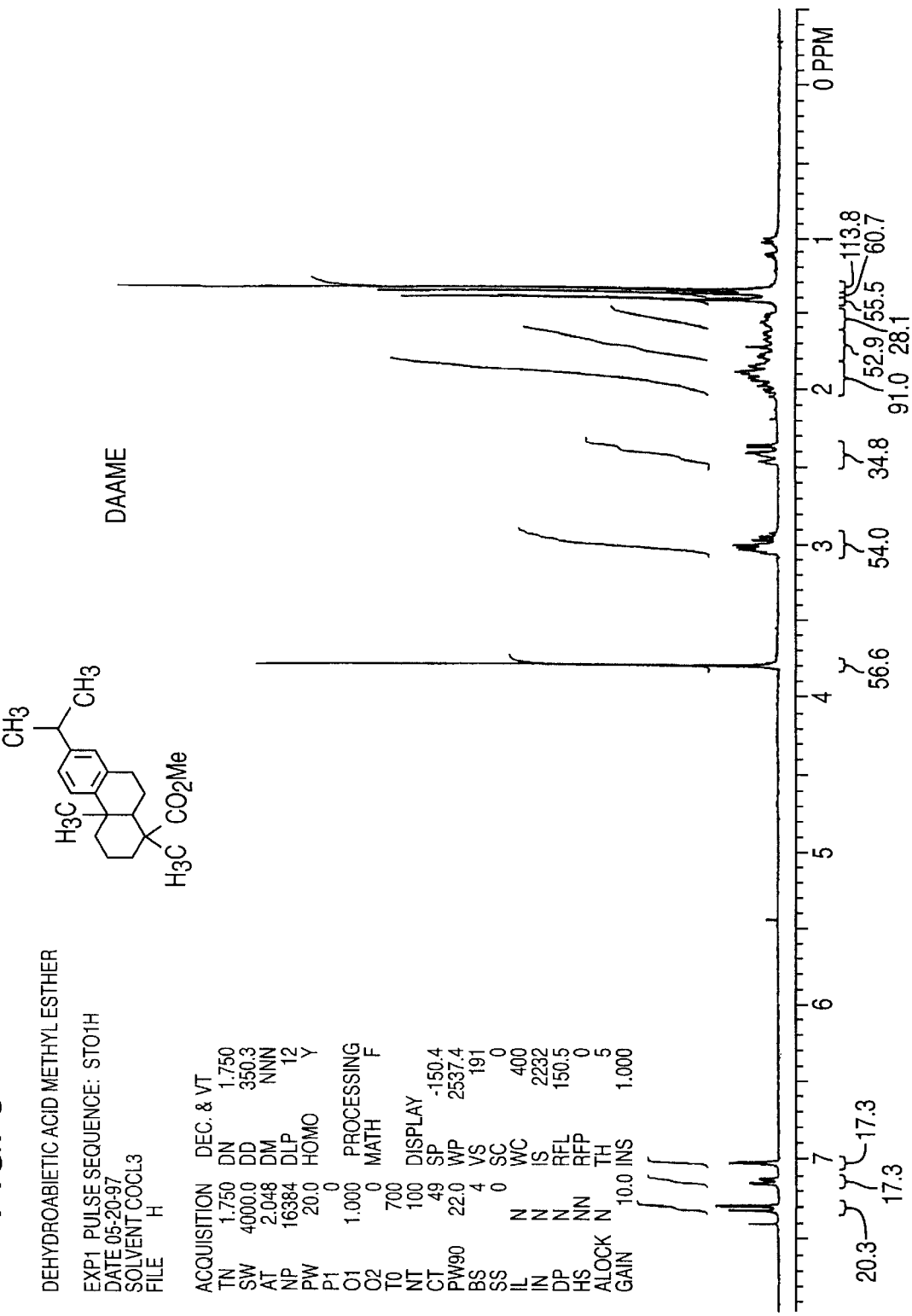
FIG. 5 is an NMR trace of synthesized DAAME.

Dehydroabietic acid (50 mg, 0.116 $\mu$mol, Helix Biotech) was dissolved in 2 ml of methanol (HPLC grade, Fisher Scientific) and cooled to 0° C. on ice in a round bottom flask. An excess (30 $\mu$mol) of ethereal diazomethane (obtained by distillation) was added and the reaction was stirred for 5 minutes. The non-reacted diazomethane was evaporated and solvent was then removed by rotary evaporation. This reaction is shown schematically in FIG. 4. The product was purified by preparative TLC (1000 $\mu$m PK6F 60 Å, Whatman) silica gel plates developed in hexane:ethyl acetate 95:5 (v:v, $R_f$: 0.25). This step provided 30 mg of a clear oil as the methyl ester that was pure by NMR (see FIG. 5). $^1$H NMR (CDCl$_3$, 300 MHz) δ1.35–1.42 (m, 12H), 1.50–2.05 (m, 7H), 2.43 (t, J=8.80 Hz, 2H), 2.90–3.05 (m, 3H), 3.80 (s, 3H), 7.02 (s, 1H), 7.14 (d, J=8.19 Hz, 1H), 7.31 (d, J=8.19 Hz, 1H). The product also gave the following electron impact mass spectra: (%) 315 (2.9, M+1), 314 (13, M), 299 (16.4), 240 (20.1), 239 (100), 197 (6.1), 173 (5.0), 141 (5.7).

1B: Synthesis of Other Esters as Lipophilic Prodrugs

Treatment of dehydroabietic acid with various aliphatic alcohols using typical Fisher esterification procedures (i. e., synthesis mixing dehydroabietic acid with an aliphatic alcohol, such as 2-propanol in acidic conditions) will readily afford aliphatic esters of dehydroabietic acid. Such esters (i. e., two to twenty carbon atoms in length possessing various substituents as described above) may provide useful prodrugs that have important pharmacological or pharmaceutical properties. For example, a palmitate or pivoyl ester of dehydroabietic acid may have a prolonged half-life compared with a simpler methyl ester. In addition, improved solubility and improved residence time for the target tissue may be obtained, as well as improved therapeutic efficacy.

1C: Synthesis of 3 Trimethylacetyl (3-Methoxy) Anilide

Cooled to 0° C. in a round bottom flask, m-anisidine (0.912 ml, 8.119 mmol) and trimethylacetyl chloride (1.205 ml, 9.743 mmol) were added by syringe to a solution of 4-dimethylaminopryidine (0.979 g, 8.119 mmol) dissolved in 30 ml of methylene chloride (HPLC grade, Fisher Scientific). The reaction was stirred 0° C. for ten minutes then stirred for ten hours at 20° C. After cooling to 0° C. approximately 1 g of ice was added to stop the reaction. Then hydrochloric acid (0.01 mmol dissolved in 10 ml of water) was added to the reaction mixture and mixed in a 100 ml separatory funnel. The methylene chloride layer was collected and then dried with sodium sulfate. The reaction was filtered with coarse Whatman filter paper then passed through a small activated carbon plug. The yield of the reaction was 1.2 g.

EXAMPLE 2
Isolation and Identification of Natural Anti-inflammatory Compounds In order to increase the likelihood that compounds with biological activity would be identified from the peat bog material, the broadest approach to the initial fractionation of the peat was used. The procedure used provided a stable and generally reproducible fractionation scheme (i.e. partitioning between acids, bases, and organic solvents, see FIG. 6) and fractionated the extract into constituent groups (i.e., fractions) of similar compounds (i.e., alkaloids, tertiary alkaloids, phenolics).

2A: Initial Fractionation of the Peat Material

Figure 6:
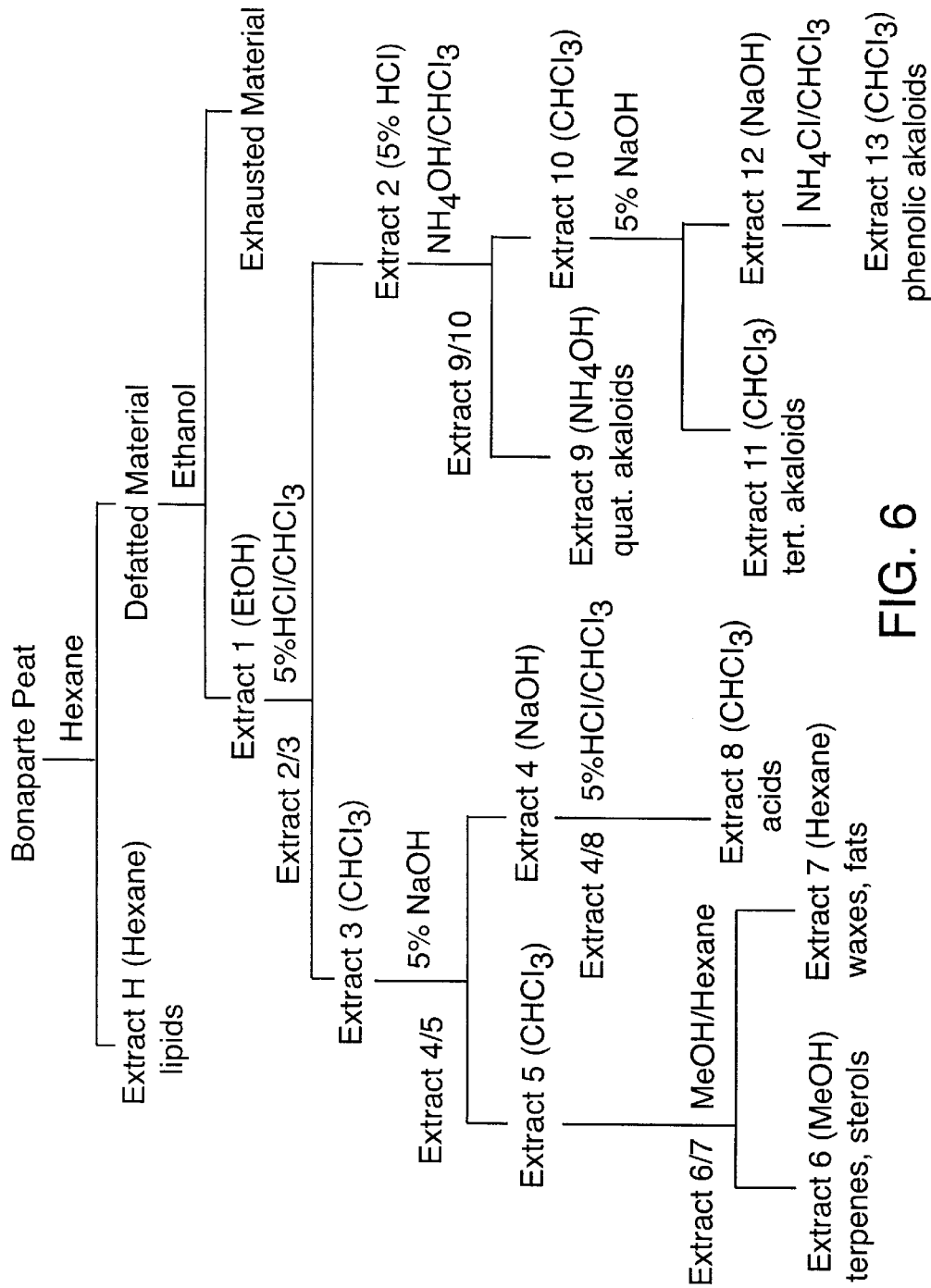
FIG. 6 diagrammatically depicts the initial chemical fractionation sequence of peat material.

The crude material was taken through a number of extraction steps to fractionate the bioactive materials. In parallel with the organic fractionation, biological activity was followed by inhibition of COX II with in vitro assays. FIG. 6 diagrammatically depicts the initial fractionation of Peat material. The fractionation scheme is described below with reference to FIG. 6.

Step 1) One kg of peat was placed in a 4 liter glass beaker and mechanically stirred by a RZR-1 (Caframo) stirrer in 1.5 L of hexane for one hour. (Note that all solvents used were HPLC grade from Fisher Scientific.) The peat was then filtered through Whatman 24 cm coarse filter paper. The eluent was evaporated and labeled Extract-H. (See FIG. 4).

Step 2) The solid material from step 1 was then mechanically stirred in 2.0 L of ethanol:water 95:5 (v/v) for 4 hours. The ethanolic/peat mixture was filtered through Whatman 24 cm coarse filter paper and the solid material was discarded. The filtrate was evaporated to approximately 275 ml and labeled Extract-1.

Step 3) The 275 ml of Extract-1 was treated with 600 ml 5% HCl and extracted with CHCl$_3$ (2×500 ml) in a separatory funnel. A light brown emulsion formed between the aqueous (Extract-2) and organic (Extract-3) layers. The aqueous layer was poured out the top and the organic layer was drained out of the bottom of the funnel. The emulsion layer was then collected and centrifuged for 10 min. at 2000×g. The supernatant was drawn off and the pellet was collected and labeled Extract-2/3.

Step 4) Extract-3 was treated with 500 ml 5% NaOH and extracted in a separatory funnel. An emulsion layer formed between the aqueous (Extract-4) and organic (Extract-5) layers. The aqueous layer was poured out the top and the organic layer was drained out of the bottom of the funnel. The emulsion layer was then collected and centrifuged for 10 min. at 2000×g. The supernatant was drawn off and the pellet was collected and labeled Extract-4/5.

Step 5) Extract-4 was treated with concentrated HCl to obtain a pH of 2.0, then extracted with CHCl$_3$ (2×500 mL) in a separatory funnel. An emulsion layer formed between the aqueous and organic (Extract-8) layers. The aqueous layer was poured out the top and the organic layer was drained out of the bottom of the funnel. The emulsion layer was then collected and centrifuged for 10 min. at 2000×g. The supernatant was drawn off and the pellet was collected and labeled Extract-4/8.

Step 6) Extract-2 (approximately 850 ml) was treated with $NH_4OH$ (30%) to obtain a pH of 9.0 and extracted with $CHCl_3$ (2×500 mL) in a separatory funnel. An emulsion layer formed between the aqueous (Extract-9) and organic (Extract-10) layers. The aqueous layer was poured out of the top and the organic layer was drained out of the bottom of the funnel. The emulsion layer was then collected and centrifuged for 10 min. at 2000×g. The supernatant was drawn off and the pellet was collected and labeled Extract-9/10.

Step 7) Extract-10 was treated with 5% NaOH (500 ml) and extracted in a separatory funnel. The organic layer was drained out of the bottom of the funnel and labeled Extract-11. The aqueous layer was collected and labeled Extract-12.

Step 8) Extract-12 was treated with 33 grams of $NH_4Cl$ (1 equivalent to NaOH present from step 7 (5%, 500 ml)), then extracted with $CHCl_3$ (2×, 250 ml) in a separatory funnel. The organic layer was collected and labeled Extract-13.

Step 9) Extract-5 was evaporated, resuspended in 100 ml of MeOH, and extracted with hexane (2×100 mL) in a separatory funnel. An emulsion layer formed between the MeOH (Extract-6) and hexane (Extract-7). The methanol layer was poured out of the top and the hexane layer was drained out of the bottom of the funnel. The emulsion layer was then collected and labeled Extract-6/7.

Step 10) All extracts were evaporated to dryness to give a mass (mg) of 67.7, 194.4, 107.4, 256.7, 21.0, 16.6, 1600.0 90.8, 99.8, 880.0, 35.6, and 11.4 for Extracts H, 2/3, 4/5, 4/8, 6/7, 9/10, 6, 7, 8, 9, 11, and 13 respectively. This procedure was repeated to process a total of 120 kg of peat.

After the initial fractionation of the peat material, the complexity and apparent stability of each extract (X-2, -2/3, -3 -4, -4/5, -4/8, -5, -6, -6/7, -7, -8, -9, -9/10, -11, -12, and -13) was assessed via TLC (see below for TLC methods). Extract 8 (X-8) was chosen for further fractionation and isolation studies based on its apparent chemical stability and chromatographic simplicity.

2B: Bioassay Analysis of Fractions Derived from the Peat Material

A bioassay-directed approach was used to chemically isolate and structurally identify possible COX II inhibitory compounds from peat extracts. To do this, fractions and sub-fractions were prepared from the peat extracts and subsequently tested in an in vitro biochemical assay utilizing a human recombinant COX II enzyme preparation described below. Those fractions exhibiting potent inhibitory activity for COX II were sub-fractionated and the ensuing fractions re-tested in the COX II assay for inhibitory activity. Using this methodology, extract X-8 was fractionated multiple times culminating in a semi-homogeneous preparation from which the structures of dehydroabietic acid methyl ester and aralkyl- and heteroalkylphenols were identified.

Both the COX I and COX II assays were performed using modified versions of previously reported methods (Corey, E. J., Shih, C., and Cashman, J. R., 1983 Proc. Natl. Acad. Sci. v80, p3; Sigal, E., Grunberger, D., Cashman, J. R., Craik, C. S., Caughey, G. H., and Nadel, J. A., 1988 Biochem. Biophys. Res Comm. v150(1), p376). To assess for the presence of compounds in the peat bog extracts that were capable of inhibiting COX II, purified human recombinant COX II (Oxford Chemical) was suspended in 50 uL of COX assay buffer (50 mM Tris, pH 8.0) containing 0.2 mM hydroquinone, 5.0 mM tryptophan, 1.0 uM hematin, and 1.0 mM glutathione. Two units of recombinant COX II enzyme (corresponding to 0.8 ug total protein) was added followed by 5 uL aliquots of the peat bog extracts yielding a final concentration of the peat extracts of 25 ug/ml. All samples were run in duplicate. To assess for inhibition of COX I, the identical procedure as outlined for COX II was followed except a ram seminal vesicle preparation enriched in COX I (Biomol) was used at a final concentration of 3.6 units of enzyme per reaction. Reactions were initiated by the addition of $^3$H-arachidonic acid (DuPont-NEN) at a final concentration of 50 uM. The reactions were maintained for 5 minutes at 37° C. and stopped by the addition of ice-cold methanol/acetic acid (10:1 v/v). The concentrations of both the enzymes (COX I and II) and the substrate ($^3$H-AA) used in these assays consistently yielded a percent conversion of arachidonic acid to the AA metabolites of approximately 50% over background in control reactions.

The assessment of cyclooxygenase activity (both COX I and II) in the presence and absence of the peat bog extracts was based on the quantitation of tlhe radiolabeled arachidonic acid metabolites prostaglandin $A_2$ ($PGA_2$), $PGE_2$, and $PGF_2$-alpha. To do this, a 50 uL sample of each reaction solution was separated via TLC on LK6DF silica plates co-spotted with arachidonic acid, $PGA_2$, and $PGF_2$-alpha and developed in hexane/isopropyl alcohol/ acetic acid (85:15:1 v/v). The bands were visualized by UV-vis or $I_2$ staining and scraped into scintillation vials for quantitation. The data was calculated assuming the activity of the minus enzyme control ($A_o$) to be 100% inhibition (0% activity) and the activity of the control group containing inhibitor solvent ($A_s$) to be 0% inhibition (100% activity). The total enzyme activity ($A_t$), the corrected enzyme activity in the presence of an inhibitor ($A_i$), and % inhibition were calculated by the following equations:

1) $A_t = A_s - A_o$

2) $A_i = A - A_o$

3) Percent Inhibition = 100 $(1 - A_i / A_t)$

EXAMPLE 3

Chemical Fractionation and Bioassay Analysis of X-8

Extract-8 (1.4 g) was initially fractionated by column chromatography on a 4.1×61 cm column with 80 g of silica gel (200–425 mesh, Aldrich). The column was equilibrated in $CH_2Cl_2$ and extract-8 was loaded in a minimum volume of $CH_2Cl_2$ (14 ml). The column was developed with a gradient of: A) $CH_2Cl_2$ (400 ml); B) $CH_2Cl_2$:MeOH 98:2 (v/v, 200 ml); C) $CH_2Cl_2$:MeOH 95:5 (v/v, 200 ml); D) $CH_2Cl_2$:MeOH 9:1 (v/v, 200 ml); E) $CH_2Cl_2$:MeOH 8:2 (v/v, 200 ml); F) $CH_2Cl_2$:MeOH 7:3 (v/v, 200 ml). Fractions (#1 to 140) of 10 ml were collected. Fractions with apparent similar composition as identified by analytical TLC were pooled. Fractions pooled were: A) fractions 1 to 33 (X-8-1); B) fractions 34 to 49 (X-8-2); C) fractions 50 to 65 (X-8-3), D) fractions 66 to 92 (X-8-4); E) fractions 93 to 140 (X-8-5). The mass recovered from each pool was 140, 84, 81, 187, and 740 mg respectively. These X-8 fractions (X-8-1 to 8-5) were subsequently tested in the COX II biochemical assay (see Table 1 below).

TABLE 1

Inhibition of Human Recombinant COX II by Fractions 8-1, -2, -3, -4, and -5.

| Fraction | Percent Inhibition of COX II |
|---|---|
| X-8-1 | 63% |
| X-8-2 | 78 |

TABLE 1-continued

Inhibition of Human Recombinant COX II by Fractions 8-1, -2, -3, -4, and -5.

| Fraction | Percent Inhibition of COX II |
|---|---|
| X-8-3 | 98 |
| X-8-4 | 100 |
| X-8-5 | 53 |

EXAMPLE 4

Identification and Isolation of Dehydroabietic Acid Methyl Ester

4A: Identification of COX II-Inhibitory Sub-Fractions of X-8

The potency of X-8-1 (63% inhibition of COX II) and material available (140 mg) warranted more chromatography to fractionate further. Methods used for chromatography are discussed above in Example 3. Fraction X-8-1 was further resolved into 6 fractions (X-8-1-1 to 6) by preparative TLC. Briefly, X-8-1 (130 mg) was loaded onto four 1000 μm PK6F 60 Å silica gel preparative TLC plates (Whatman) and developed in $CH_2Cl_2$:MeOH 98:2 (v/v). Bands were visualized by illumination at 254 nm and individually collected. The collected fractions had Rf values of 0-0.23 (X-8-1-1), 0.23–0.25 (X-8-1-2), 0.25–0.33 (X-8-1-3), 0.33–0.44 (X-8-1-4, 0.44–0.78 (X-8-1-5), and 0.78–0.90 (X-8-1-6). The organic material was removed from the silica gel by stirring in $CH_2Cl_2$:MeOH 9:1 (v/v) and then filtered. The mass recovered from each fraction was 33, 18, 23, 22, 15, and 8 mg respectively. The inhibitory potency of each X-8-1 sub-fraction was accessed using the COX-II biochemical assay, showing 1.6, −3.2, −17, −4, 24, and 17% inhibition for fractions X-8-1-1 to X-8-1-6, respectively, as presented in Table 2.

TABLE 2

Inhibition of Human Recombinant COX II by Fractions 8-1-1, -2, -3, -4, -5, and -6.

| Fraction | Percent Inhibition of COX II |
|---|---|
| X-8-1-1 | 1.6% |
| X-8-1-2 | −3.2 |
| X-8-1-3 | −17 |
| X-8-1-4 | −4 |
| X-8-1-5 | 24 |
| X-8-1-6 | 17 |

The potency of X-8-1-5 (24% inhibition of COX II) and the mass available (14 mg) warranted further fractionation. Methods used for chromatography of X-8-1-5 are described above in Example 3. Fraction X-8-1-5 was further resolved into 6 fractions (X-8-1-1 to 6) by preparative TLC. X-8-1-5 (12 mg) was loaded onto 1000 μm PK6F 60 Å silica gel preparative TLC plate (Whatman) and developed in hexane-:ethyl acetate 3:1 (v/v). Bands were visualized at 254 nm and individually collected. The collected fractions had Rf values 0–0.06 (X-8-1-5-1), 0.06–0.12 (X-8-1-5-2), 0.12–0.19 (X-8-1-5-3), 0.19–0.51 (X-8-1-5-4), 0.51–0.61 (X-8-1-5-5), and 0.61–0.89 (X-8-1-5-6). The organic material was removed from the silica gel by stirring in the developing solvent mixture and then filtering. The mass recovered from each fraction was 1.3, 3.5, 1.5, 3.9, 0.5, and 1.9 mg respectively.

These sub-fractions were then tested for inhibitory activity using the COX II biochemical assay, with fractions X-8-1-5-1 to X-8-1-5-6 showing 38, 41, 39, 32, 72, and 51% inhibition, respectively, as presented in Table 3.

TABLE 3

Inhibition of Human Recombinant COX II by Fractions 8-1-5-1, -2, -3, -4, -5, and -6.

| Fraction | Percent Inhibition of COX II |
|---|---|
| X-8-1-5-1 | 38% |
| X-8-1-5-2 | 41 |
| X-8-1-5-3 | 39 |
| X-8-1-5-4 | 32 |
| X-8-1-5-5 | 72 |
| X-8-1-5-6 | 51 |

4B: Identification of Dehydroabietic Acid Methyl Ester Based on GCMS and MS Data Fraction X-8-1-5-5 had 72% inhibition in the biochemical COX II assay, warranting further studies to identify the compound responsible for the inhibitory activity. GC-MS was performed on X-8-1-5-5 with a Micromass Trio 2000 Quadrapole Mass Spectrometer in the Electron Impact Ionization mode coupled to a Hewlett Packard 5890 Gas Chromatograph. Sampling was performed using a Hewlett-Packard 7673A Autosampler. For data handling 100 MHz 486 PC and Windows based Micromass MassLynX® and MaxEnt® software were used. Gas chromatographs were performed using helium as the carrier gas with J and W DB-5W, 30 meter column. Oven temperature program used is as follows. First minute from ambient temperature to 40° C. at 15° C. per minute. Next 8 minutes increasing from 40° C. to 280° C. at 10° C. per minute, and the next 6 minutes decreasing from 280° C. to ambient temperature.

Figure 7:
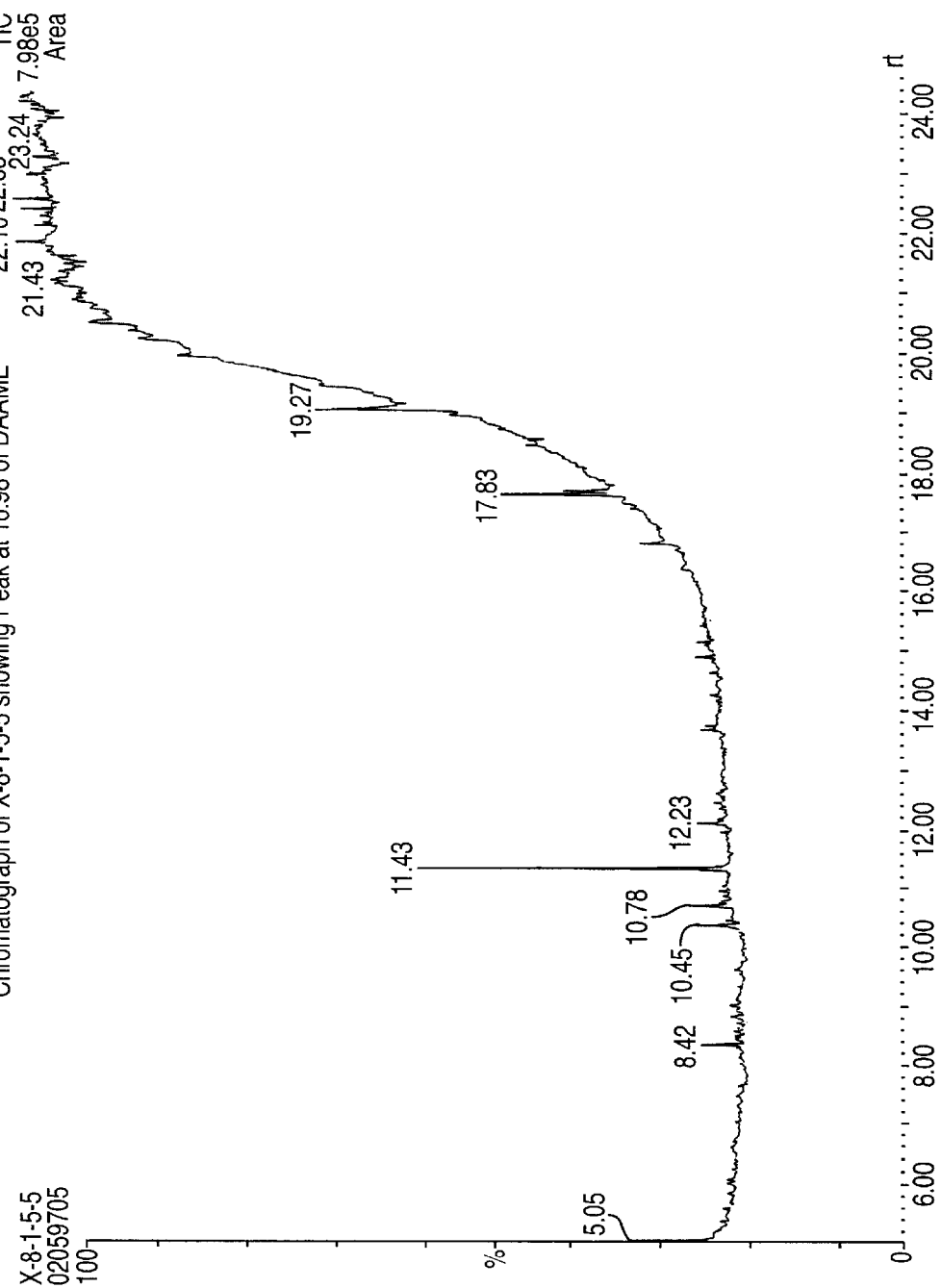
FIG. 7 is a chromatograph of fraction X-8-1-5-5 showing the DAAME 16.98 minute peak.
Figure 8:
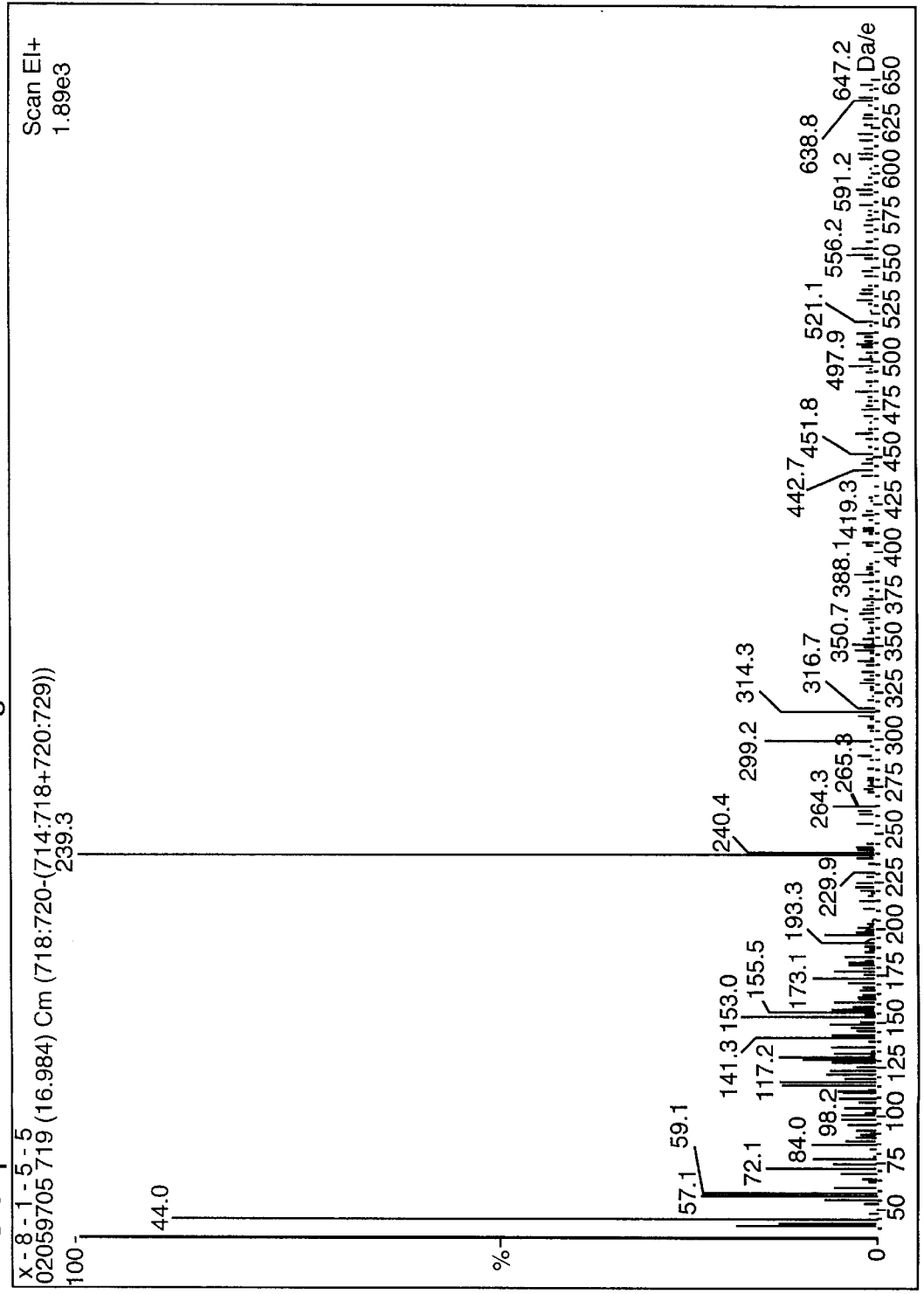
FIG. 8 is a mass spectrum of the 16.98 minute peak fraction shown in the chromatograph of FIG. 7.
Figure 9:
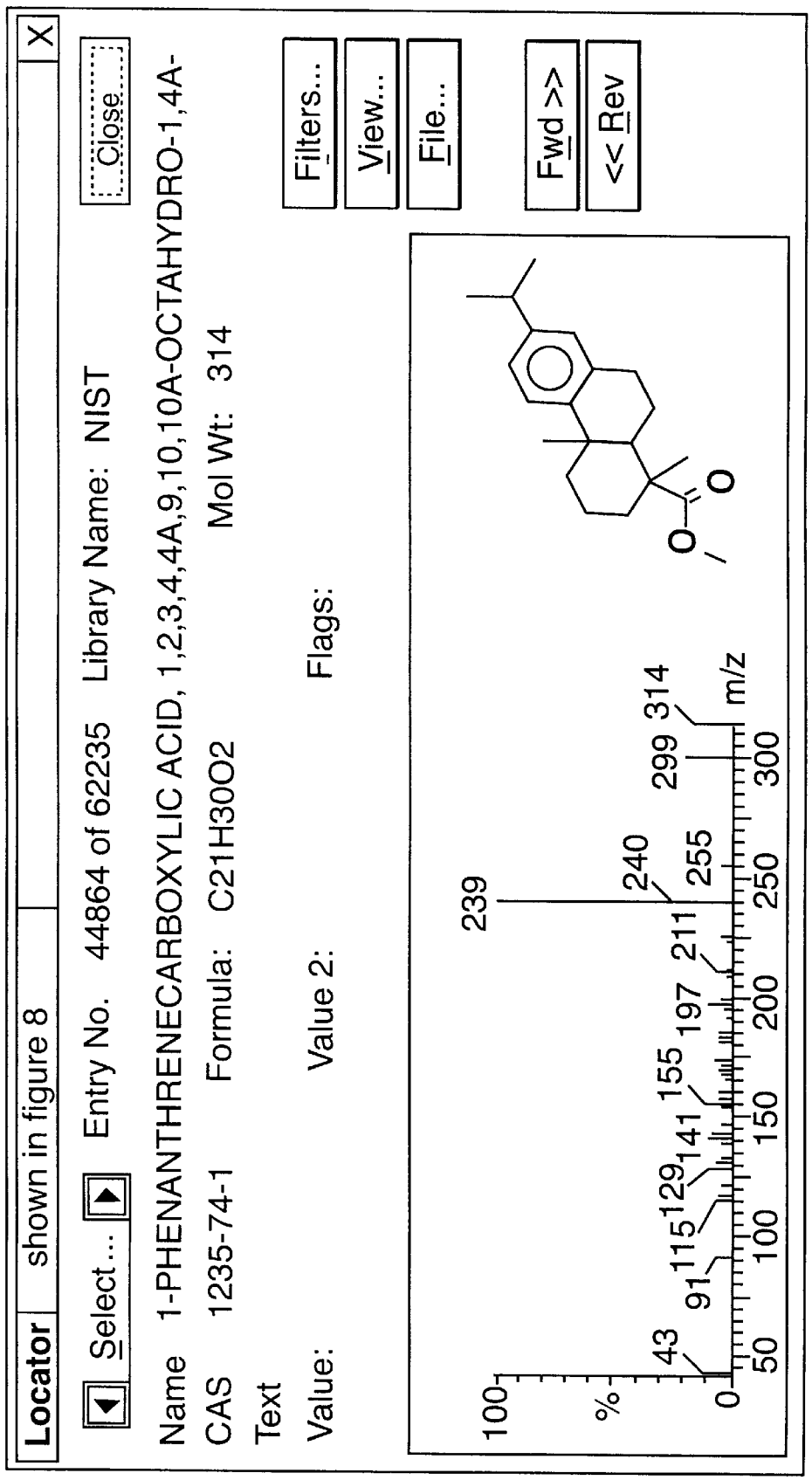
FIG. 9 is a mass spectrum of DAAME, taken from the NIST Library of mass spectra, that matches the mass spectrum of FIG. 8.

In fraction X-8-1-5-5 the peak at 16.98 minutes retention time in the chromatograph shown in FIG. 7 gave a mass spectrum shown in FIG. 8 that was matched with mass spectrum of dehydroabietic acid methyl ester from the NIST Library of mass spectra shown in FIG. 9.

EXAMPLE 5

Characterization of the Inhibitory Activity of Dehydroabietic Methyl Ester Using Biochemical COX I, COX II, and 15-LO Assays The inhibitory activity of dehydroabietic acid methyl ester was assessed by performing biochemical assays that utilized 1) human recombinant COX II, 2) ovine COX I, and 3) rabbit reticulocyte 15-LO. In all biochemical assays dehydroabietic acid methyl ester and inhibitory control compounds were used at a final concentration of 250 μm. The COX I and II biochemical assays have been previously described in this document (see COX I and II Assays Used to Test X-8 Fractions and Purified Compounds, Example 3). The 15-LO assay was done using a modified version of a previously reported method (Corey, E. J., Shih, C., and Cashman, J. R. (1983) Proc. Natl. Acad. Sci. v80, p3,581; Sigal, E., Grunberger, D., Cashman, J. R., Craik, C. S., Caughey, G. H., and Nadel, J. A. (1988) Biochem. Biophys. Res Comm. v150(1), p376). Briefly, 24.5 units of a rabbit reticulocyte 15-LO preparation (corresponding to 7 ug total protein)(Oxford Biochemicals) was placed in potassium phosphate buffer (10 mM, pH 6.0). Dehydroabietic acid methyl ester was added to give a final concentration of 250 uM. The reaction was initiated by the addition of $^3$H-AA (50 uM final concentration) and maintained at 37° C., for 5 min. The reaction was stopped by the addition of ice-cold methanol containing $NaCNBH_3$ (to reduce peroxides). A portion of each reaction solution was then separated via TLC (250

μm PK6F 60 Å silica gel preparative TLC plate, Whatman), co-spotted with AA and 15-HETE (a metabolic product of 15-LO) and developed in hexane/ether/acetic acid (50:50:1) to separate 15-HETE from AA (Rf=0.29 and 0.5, respectively). Bands on the TLC plates were then visualized by $I_2$ and scraped for quantitation. As with the COX I and II assays, percent inhibition was calculated based on a comparison between incubations performed in the presence and absence of dehydroabietic acid methyl ester (see "Fractionation and Bioassay Analysis of Fractions Derived from Extract-8" above).

Using the COX I, COX II, and 15-LO biochemical assays, the inhibitory activity of dehydroabietic acid methyl ester was determined. Previous studies with the COX I and II assays indicated that known COX II inhibitory compounds such as Nimesulide (Cayman Chemical) had to be used at a final concentration of 250 uM to observe inhibition (see Table 4). Due to the apparent insensitivity of the COX II assay, all compounds (control and dehydroabietic acid methyl ester) were added to the reaction mixture to give a final concentration of 250 uM. Dehydroabietic acid methyl ester inhibited COX II preferentially over COX I by over 30%. In addition, dehydroabietic acid methyl ester increased the enzymatic activity of 15-LO by over 93%. The results of these studies are shown in Table 4.

TABLE 4

Percent Inhibition of COX I, COX II, and 15-LO by Dehydroabietic Acid Methyl Ester

| Compound | Enzyme Assay | | |
|---|---|---|---|
| | COX I | COX II | 15-LO |
| 1) Dehydroabietic acid methyl ester | 0.2% | 31.5% | −93.6% |
| 2) Nimesulide (COX II-Specific Inhibitor) | | 13.3% | |

EXAMPLE 6

Assessment of the Biological Activity and Cytotoxicity of Dehydroabietic Acid Methyl Ester Using Cell-Based Assays 6A: Cell-Based COX II and 5-LO Assays The ability of dehydroabietic acid methyl ester to inhibit the enzymatic activities of COX II and 5-LO was tested using primary cultures of human foreskin keratinocytes. Briefly, human keratinocytes were plated in 48-well plates (Nunc) at an initial density of $2.5 \times 10^4$ cells per well. The cultures were maintained in medium 154XP (Cascade Biologics) to which human keratinocyte growth supplement (Cascade Biologics) was added. Cultures were plated initially in medium 154XP containing 0.07 mM $CaCl_2$. Upon reaching ~70% confluency, the media was exchanged with high calcium medium 154XP containing 1.2 mM $CaCl_2$. Previous studies have shown that an increase in extracellular $Ca^{2+}$ concentration induces the differentiation of cultured keratinocytes with a concomitant increase in the expression of COX II protein and COX II mRNA with no apparent effect on COX I expression (Leong, J., Hughes-Fulford, M., Rakhlin, A., Maclouf, J., and Goldyne, M., (1996), Exp. Cell Res., V224, p79). Twenty-four hours after switching to the high calcium media, duplicate wells were treated with dehydroabietic acid methyl ester serially diluted in ethanol to produce final concentrations of 5, 1.0, 0.2, and 0.04 uM. Companion cultures were treated with an identical dilution series of the Merck COX II-specific inhibitor DFU. Twenty-four hours later, samples were removed from each treated well (as well as vehicle-treated control wells) and the amount of $PGE_2$ (a product of the COX II pathway) was quantified using a $PGE_2$-specific enzyme immunoassay (Cayman Chemical). ), As was done with the previously described biochemical assays (COX I, COX II, 5-LO, and 15-LO), the percent inhibition was calculated based on a comparison between vehicle treated control cultures and cultures treated with dehydroabietic acid methyl ester or DFU (see Fractionation and Bioassay Analysis of Fractions Derived from Extract-8 above).

Figure 10:
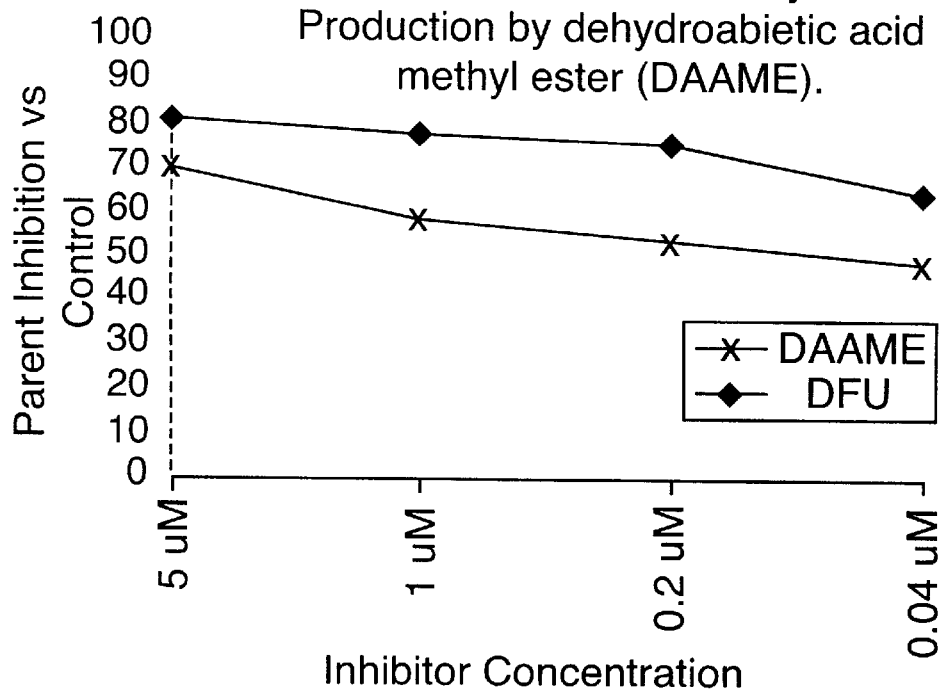
FIG. 10 graphically presents the results of an assay showing the inhibition of human keritinocyte $PGE_2$ production by DAAME.

As shown in FIG. 10, dehydroabietic acid methyl ester inhibited the production of $PGE_2$ by cultured human keratinocytes. The degree of inhibition was dependent on the concentration of dehydroabietic acid methyl ester added to the culture. Dose-dependent inhibition was also observed with the COX II-specific inhibitor DFU from Merck.

In addition to assessing the effect of dehydroabietic acid methyl ester on the production of $PGE_2$ by human keratinocytes, the human keratinocyte culture system was also used to assess for the inhibition of $LTB_4$ production. Keratinocytes have not been used as extensively as other cell types for 5-LO studies, however, human keratinocytes produce appreciable amounts of $LTB_4$ and production of this eicosanoid by cultured keratinocytes is inhibited by known inhibitors of 5-LO (see FIG. 11).

To assess for inhibition of $LTB_4$ production, human keratinocytes were cultured as described above. Following introduction of the high calcium media, the identical dilution series of dehydroabietic acid methyl ester as described above in the PGE2 study was added to duplicate wells of keratinocytes. Twenty-four hours later culture media samples were removed from each well and the amount of $LTB_4$ in each sample determined using an enzyme immunoassay specific for $LTB_4$ (Cayman Chemical). As was done with the $PGE_2$ assay described above, the percent inhibition was calculated based on a comparison between vehicle treated control cultures and cultures treated with dehydroabietic acid methyl ester or Rev 5901 (a specific 5-LO inhibitor; Cayman Chemical).

Figure 11:
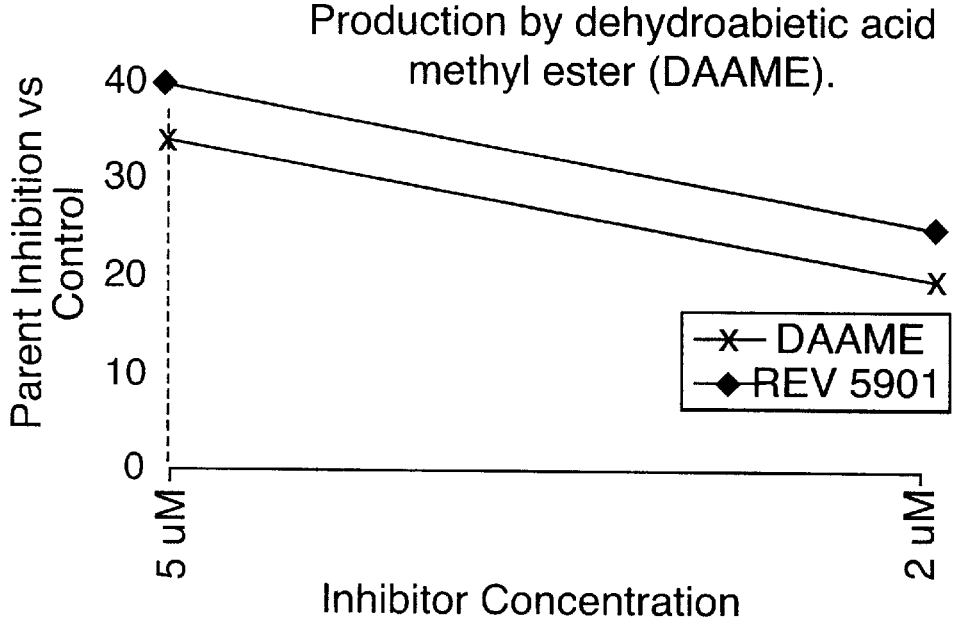
FIG. 11 graphically presents the results of an assay showing the inhibition of human keratinocyte $LTB_4$ production by DAAME.

As shown in FIG. 11, dehydroabietic acid methyl ester inhibited the production of $LTB_4$ by cultured human keratinocytes in a dose-dependent manner. Such dose-dependent inhibition was also observed with the 5-LO-specific inhibitor REV 5901. The combined inhibition of both $PGE_2$ (see FIG. 10) and $LTB_4$ (see FIG. 11) production by cultured human keratinocytes suggests that dehydroabietic acid methyl ester acts as a dual COX II/5-LO inhibitor.

6B: Cytotoxicity of Dehydroabietic Acid Methyl Ester

To address the possibility that the inhibition of both $PGE_2$ and $LTB_4$ production by human keratinocytes treated with dehydroabietic acid methyl ester was not due to toxicity, a cell lactate dehydrogenase toxicity assay (Fisher Scientific) was performed. Briefly, lactate dehydrogenase (LDH) is found intracellularly and is released only in response to toxic stimuli and/or cell death. The amount of LDH released into the media of cultured cells is indicative of the degree of toxicity occurring in that culture. To do the assay, 48-well plates of cultured human keratinocytes (as described above for the $PGE_2$ assay) were prepared and treated with the same concentrations of dehydroabietic acid methyl ester as described above for the $PGE_2$ and $LTB_4$ assays. One hour prior to harvesting culture media samples from wells treated with dehydroabietic acid methyl ester, duplicate wells were treated with a cell lysis buffer (Fisher Scientific) that caused 100% cell death to occur in the treated wells. After culture media samples were collected from all wells, the amount of LDH present in each was determined using a colorometric assay (Fisher Scientific). The amount of LDH present in media samples taken from well treated with lysis buffer was assumed to be 100%. The amount of LDH released into the media of cultures treated with dehydroabietic acid methyl ester as well as vehicle-control media was determined using the colorometric assay and expressed as a percentage of that released by the 100% cell death wells.

Figure 12:
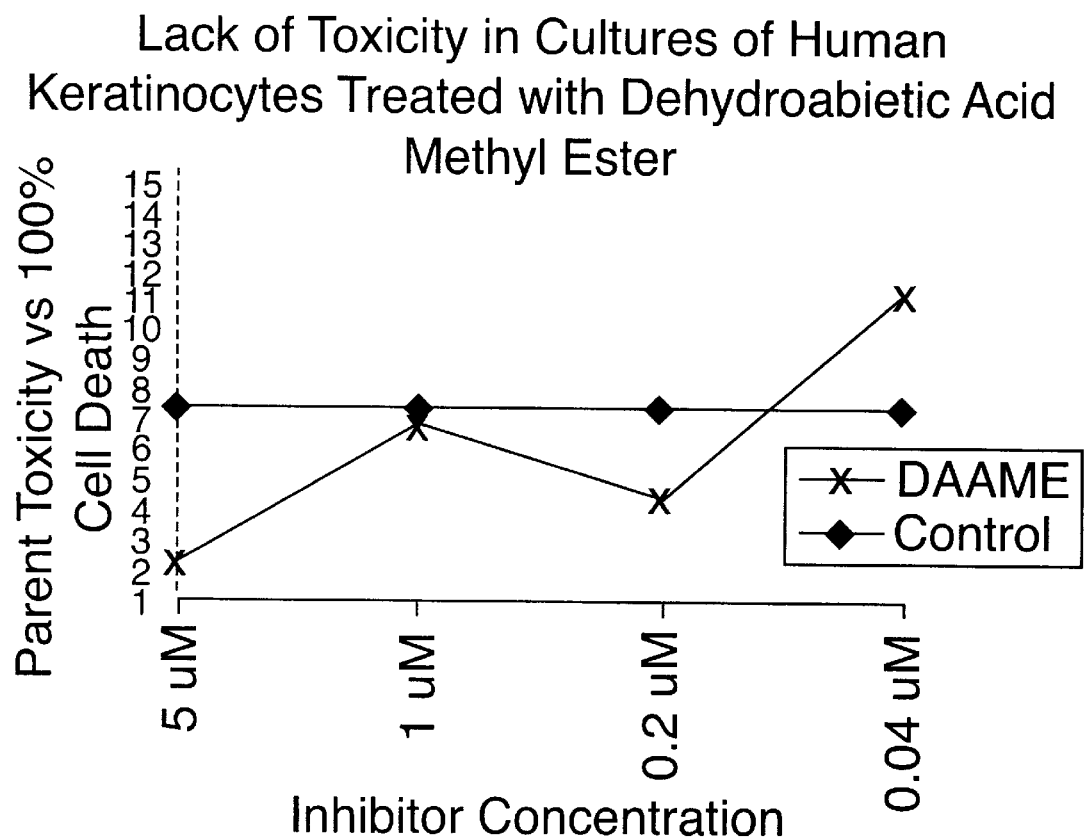
FIG. 12 graphically presents the results of an assay showing the lack of toxicity in cultures of human keratinocytes treated with DAAME.

Vehicle treated control cultures exhibited percent toxicities ranging from 2 to 15% versus the 100% cell death control. No culture treated with dehydroabietic acid methyl ester exhibited a percent toxicity greater than 12% versus the cell death control (FIG. 12). As shown in FIG. 12, the percent toxicities determined for cultures treated with dehydroabietic acid methyl ester was independent of the concentration of dehydroabietic acid methyl ester used to treat the culture. The lack of appreciable toxicity in cultures treated with dehydroabietic acid methyl ester is consistent with the lack of toxicity when treated cultures were examined microscopically.

EXAMPLE 7
Identification of COX II-Inhibitory Fractions of the Peat Material Containing Aralkyl- and Heteroalkylphenols
7A: Fractions Showing High COX II Inhibitory Activity Using a similar bioassay-directed fractionation scheme as used to identify dehydroabietic methyl ester, multiple fractions and sub-fractions derived from extract 8 were assessed for the presence of anti-inflammatory compounds by assessing their ability to inhibit the activity of COX II using an identical protocol as that described in Example 2B (above). Fractions and sub-fractions found to inhibit COX II were subjected to structural analysis in an attempt to identify the compound(s) responsible for the inhibitory activity. Two fractions in particular showed potent COX II inhibitory activity. These fractions and the percent inhibition of COX II obtained with each is shown in Table 5.

TABLE 5

Percent Inhibition of COX II by Sub-fractions of Extract 8.

| Fraction | Percent Inhibition of COX II |
| --- | --- |
| X-8-1-5-5 | 72% |
| X-8-5-1-6-2 | 29.3 |

Figure 13:
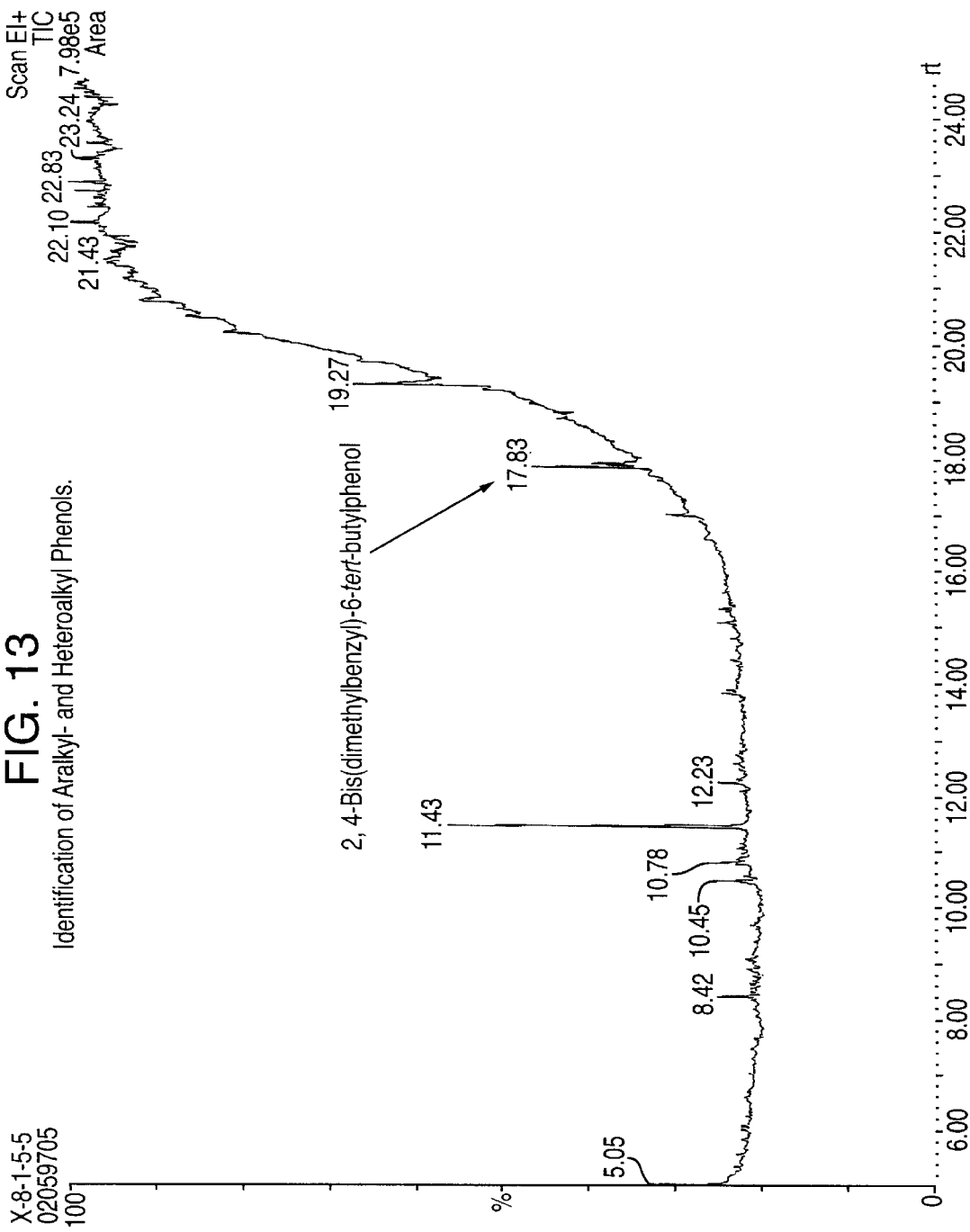
FIG. 13 is a chromatograph of fraction X-8-1-5-5 showing the peaks identified as aralkylphenols and heteroalkylphenols.
Figure 14:
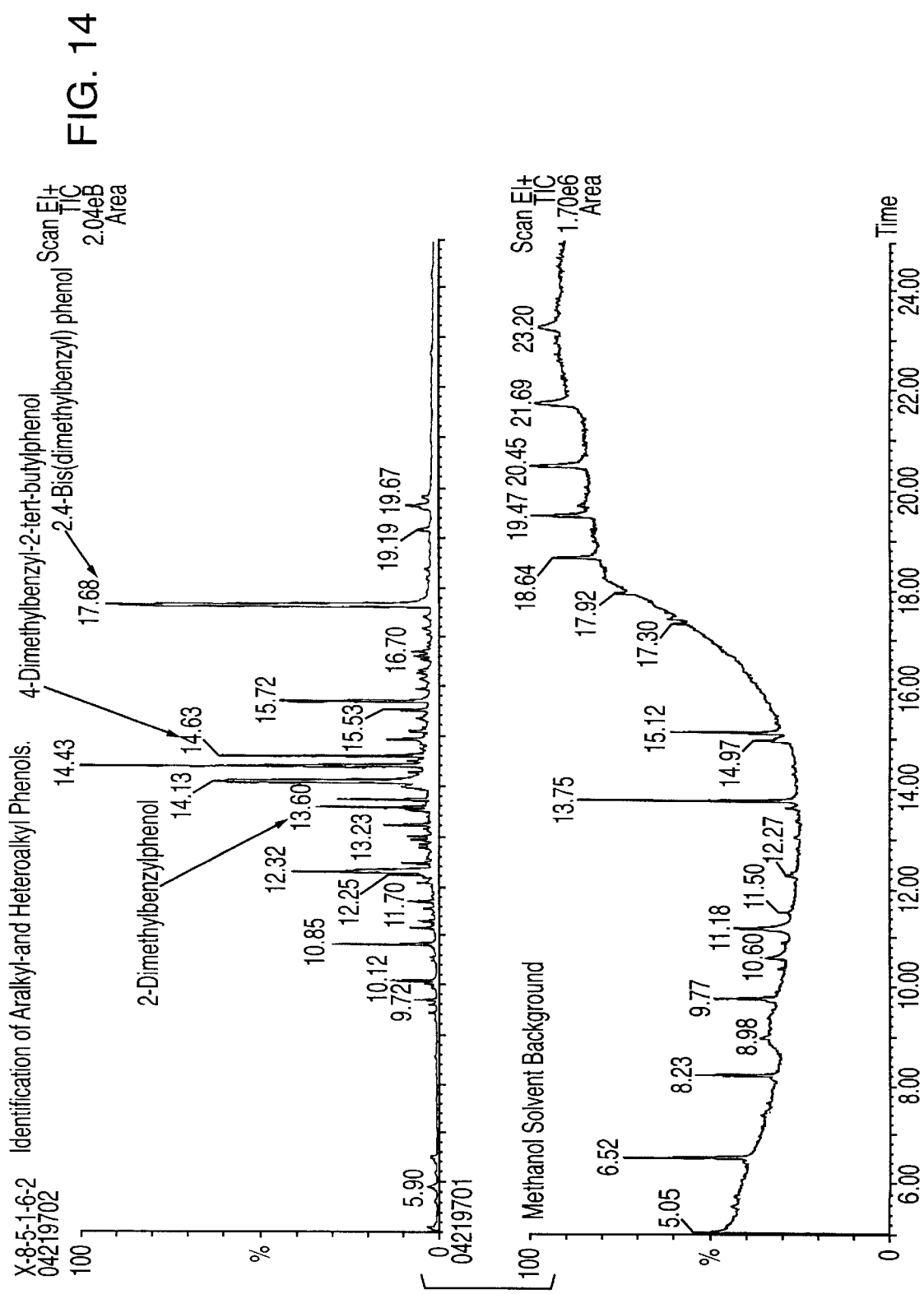
FIG. 14 is a chromatograph of fraction X-8-5-1-6-2 showing the peaks identified as aralkylphenols and heteroalkylphenols.
Figure 15:
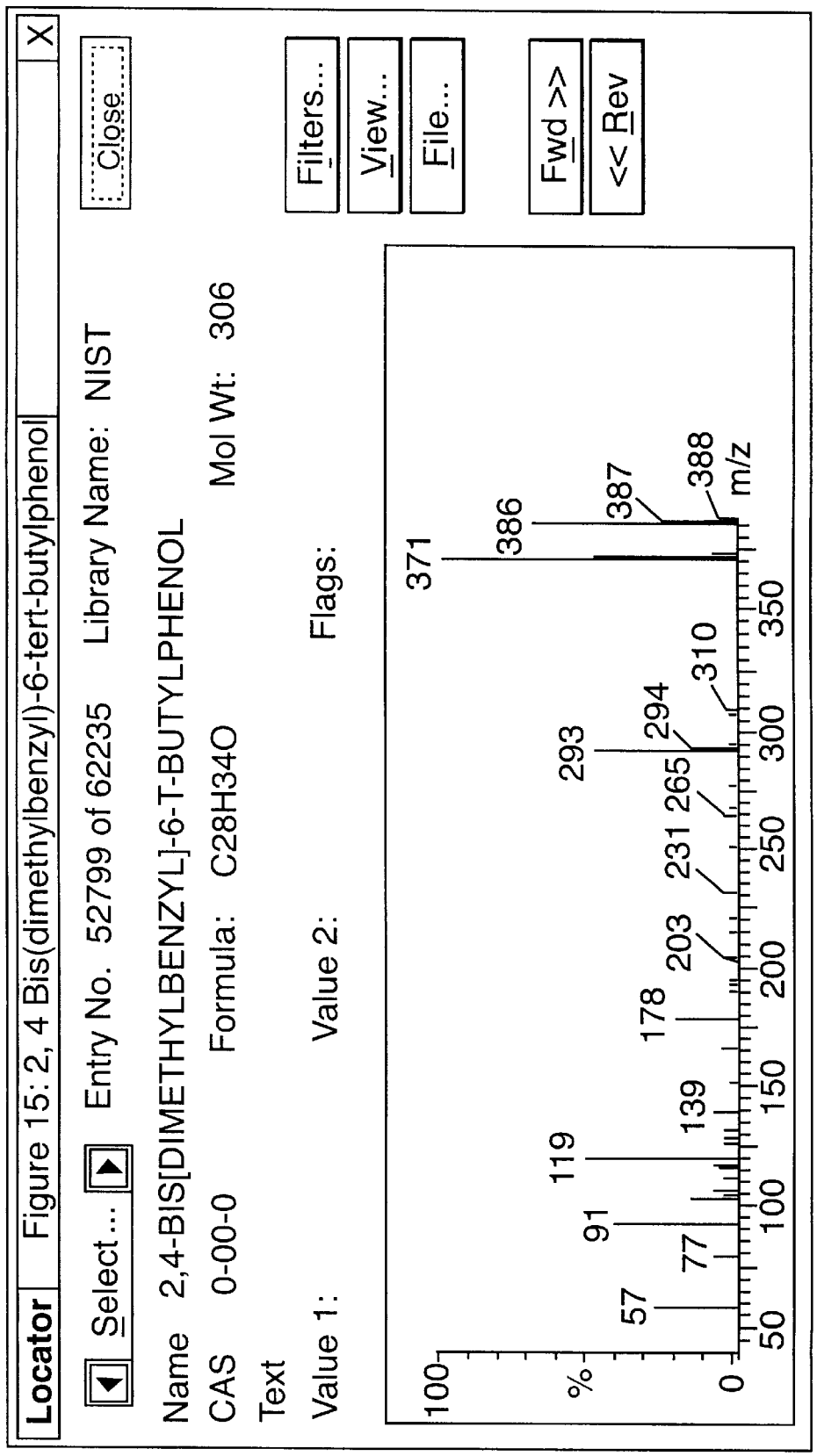
FIG. 15 is a mass spectrum from the NIST Library showing 2,4-Bis(dimethylbenzyl)-6-tert-butyphenol.
Figure 16:
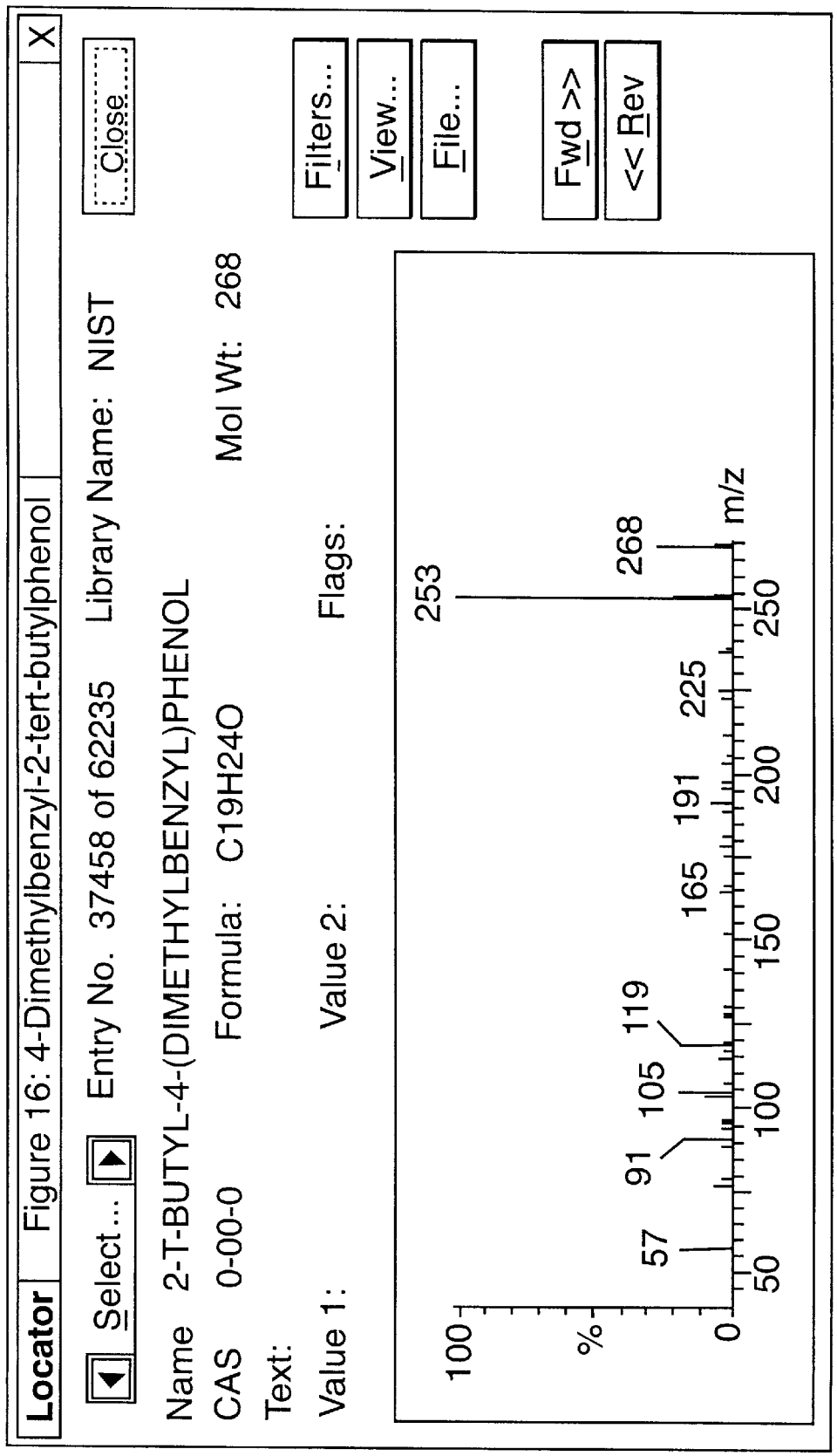
FIG. 16 is a mass spectrum, taken from the NIST Library, showing 4-dimethylbenzyl-2-tert-butyphenol.
Figure 17:
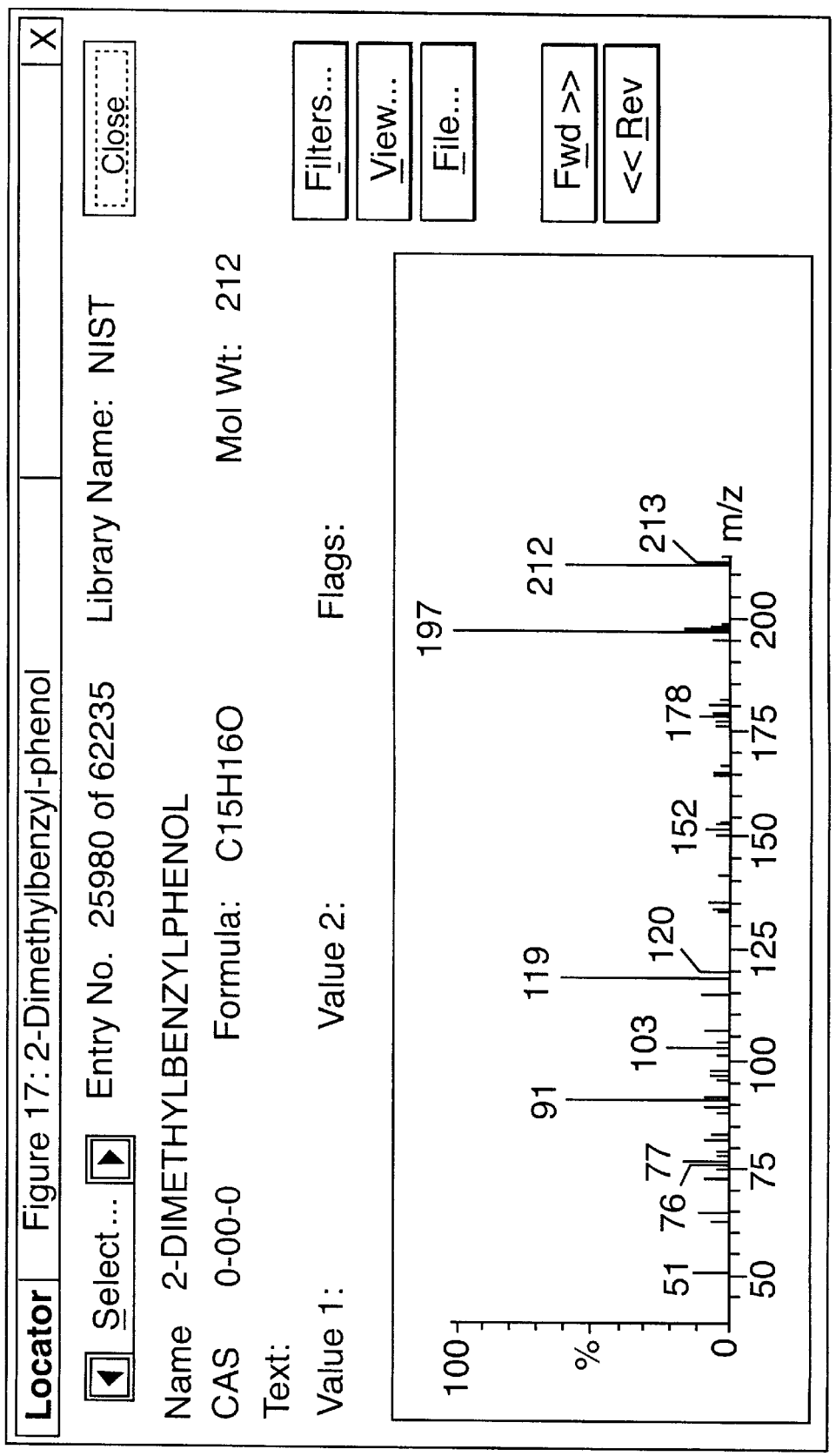
FIG. 17 is a mass spectrum, taken from the NIST Library, showing 2-dimethylbenzylphenol.
Figure 18:
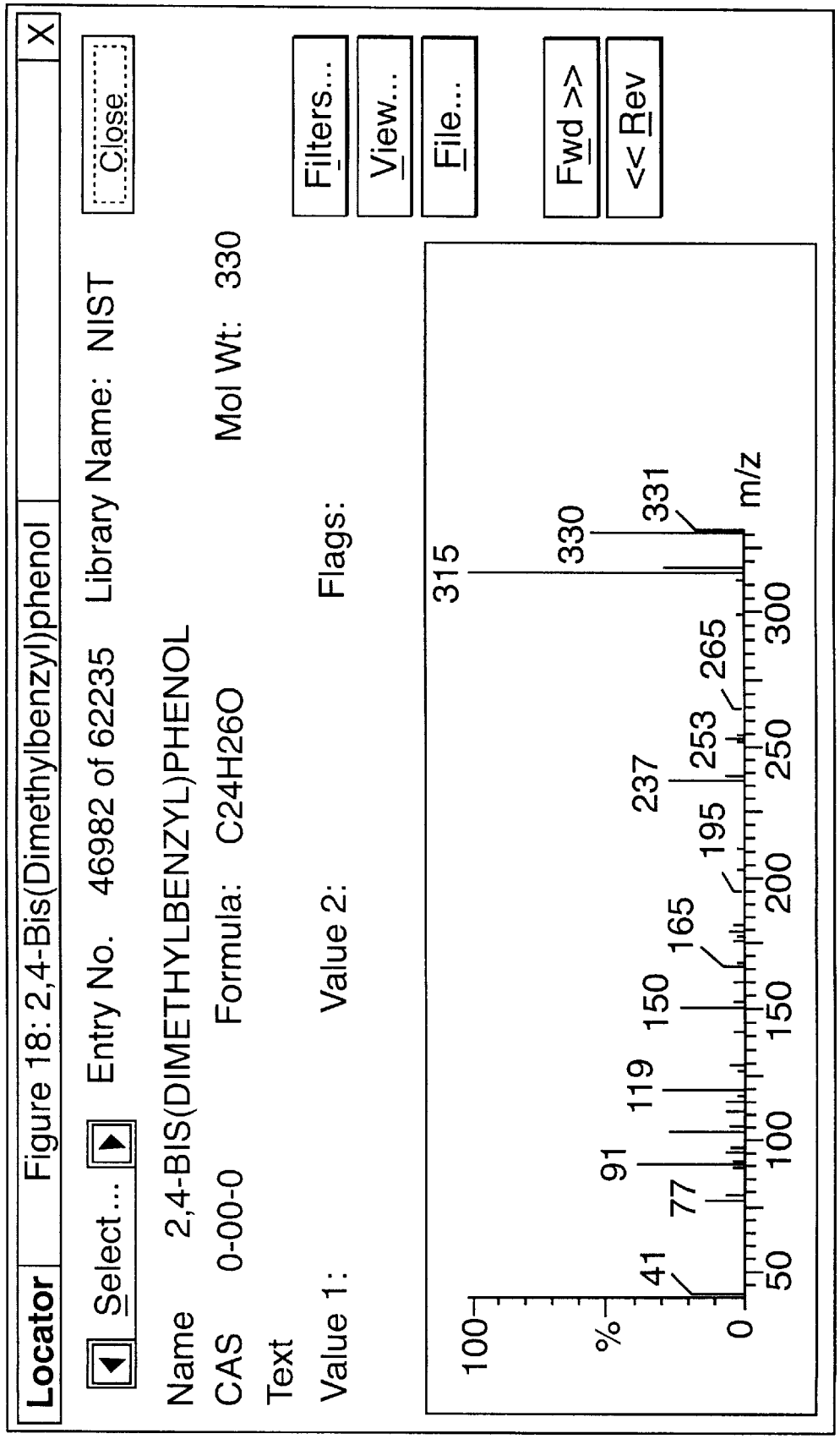
FIG. 18 is a mass spectrum, taken from the NIST Library, showing 2,4-Bis(dimethylbeiizyl) phenol.

EXAMPLE 7B
Identification of Aralkyl- and Heteroalkyl Phenols in COX II Inhibitory Fractions Using GCMS and MS GC-MS was performed on fractions X-8-1-5-5 and X-8-5-1-6-2 with a Micromass Trio 2000 Quadrapole Mass Spectrometer in the Electron Impact Ionization mode coupled to a Hewlett Packard 5890 Gas Chromatograph. Sampling was performed using a Hewlett-Packard 7673A Autosampler. For data handling a 100 MHz 486 PC and Windows based Micromass MassLynx® and MaxEnt® software were used. Gas chromatographs were performed using Helium as the carrier gas with a J and W DB-5W, 30 meter column. Once spectra from these fractions was obtained, peaks in the chromatograms were identified using the NIST library of mass spectra. Aralkyl- and heteroalkyl phenols were identified in two separate fractions (X-8-1-5-5 and X-8-5-1-6-2) that exhibited potent inhibition of COX II. Fraction X-8-1-5-5 is the fraction from which dehydroabietic acid methyl ester was identified (see Section I" above). The aralkylphenol and heteroalkylphenol compounds and the COX II inhibiting fractions from which they were identified are detailed in Table 6. The chromatograms of X-8-1-5-5 and X-8-5-1-6-2 showing the peaks identified as aralkylphenol and heteroalkylphenol phenols is shown in FIGS. 13 and 14 respectively. The mass spectra of the compounds detailed in Table 6 (below) were obtained from the NIST Library of mass spectra shown in FIGS. 15–18.

TABLE 6

Identification of Aralkyl- and Heteroalkylphenols from COX II Inhibitory Fractions.

| Compound | COX-II Inhibitory Fraction |
| --- | --- |
| 1) 2-4-Bis(dimethylbenzyl)-6-tert-butylphenol | X-8-1-5-5 |
| 2) 4-Dimethylbenzyl-2-tert-butylphenol | X-8-1-5-5 and X-8-5-1-6-2 |
| 3) 2-Dimethylbenzylphenol | X-8-5-1-6-2 |
| 4) 2,4-Bis(dimethylbenzyl)phenol | X-8-5-1-6-2 |

EXAMPLE 8
Isolation and Identification of 4-Dimethyl-benzylphenol (4-Cumylphenol)
8A: Fractionation and Bioassay Analysis of Wingstay-C; A Commercially Available Source of Bis(dimethylbenzyl)-6-tert-butylphenol GCMS analysis of fraction X-8-1-5-5 indicated the presence of 2-4-Bis(dimethylbenzyl)-6-tert-butyl-phenol. Given the high inhibition of COX II observed with this fraction (72%; see Table 5) and the presence of aralkyl- and heteroalkylphenols in another COX II inhibitory fraction (X-8-5-1-6-2), a commercially available preparation (Wing stay-C; Goodyear Tire and Rubber Company) reported to contain 2-4-Bis(dimethylbenzyl)-6-tert-butyl-phenol was obtained. Preliminary analysis of the Wingstay C preparation was conducted via TLC. Briefly, the Wingstay preparation was fractionated sequentially using dry-column chromatography followed by conventional TLC. To do this, Wingstay C (7.5 g) was initially fractionated by dry silica column chromatography in a 17 by 2.04 cm dialysis tube (Spectrapore membrane tubing, MWCO 12–14,000) developed in hexane:$CH_2Cl_2$ 9:1 (v:v, 100 ml). An orange band (fraction 1) and a yellow band (fraction 2) developed in the column. Each fraction was cut out of the dialysis tubing and the organic material was removed from the silica by stirring in $CH_2Cl_2$ and filtering. This procedure was repeated with another 7.5 g of Wingstay C to produce a total of 407.7 mg of fraction 1 (WC-1) and 9.9632 mg of fraction 2 (WC-2).

Based on the apparent complexity and chemical nature of the compounds present in WC-1 (as judged by TLC), this fraction (400 mg) was further resolved into 10 fractions by column chromatography in a 30 g silica gel (200–425 mesh, Aldrich) column equilibrated in hexane:$CH_2Cl_2$ 3:1 (v:v). The column was developed in a gradient of A) hexane:$CH_2Cl_2$ 3:1 (v:v, 250 ml); B) hexane:$CH_2Cl_2$ 1:1 (v:v, 250 ml); C) hexane:$CH_2Cl_2$ 1:3 (v:v, 250 ml); and D) $CH_2Cl_2$ (250 ml). Fractions (#1 to 100) of 10 ml were collected. Fractions with apparent similar composition as identified by analytical TLC were pooled. Fractions pooled were: 1) fractions 1 to 12 (WC-1-1); 2) fractions 13 to 24 (WC-1-2); 3) fractions 25 to 32 (WC-1-3); 4) fractions 33 to 41 (WC-1-4); 5) fractions 42 to 50 (WC- 1-5); 6) fractions 51 to 70 (WC-1-6); 7) fractions 71 to 75 (WC-1-7); 8) fractions 76 to 79 (WC-1-8); 9) fraction 80 (WC-1-8); and fractions 81 to 100 (WC-1-10). The mass recovered from each pool was 45.6, 1.1, 1.3, 1.7, 1.2, 204.3, 28.7, 13.2, 9.0, and 1.0 mg respectively.

8B: Identification of 4-Cumylphenol in COX II Inhibitory Fractions of the Wingstay C Preparation Wingstay fractions WC-1-1 to WC-1-10 were assessed for the presence of anti-inflammatory activity by assessing the ability of each fraction to inhibit the enzymatic activity of human recombinant COX II. The methods used to test for the inhibition of COX II by the Wingstay fractions was identical to that described in Example 2B. The percent inhibition of COX II caused by WC-1 to WC-10 is shown below in Table 7.

TABLE 7

Percent Inhibition of COX II by Sub-fractions of Wingstay-C.

| Fraction | Percent Inhibition of COX II |
| --- | --- |
| WC-1-1 | 26.8% |
| WC-1-2 | 8.7 |
| WC-1-3 | 16.7 |
| WC-1-4 | 12.0 |
| WC-1-5 | 48.5 |
| WC-1-6 | 52.4 |
| WC-1-7 | 26.2 |
| WC-1-8 | 23.6 |
| WC-1-9 | 12.1 |
| WC-1-10 | 5.4 |

Figure 19:
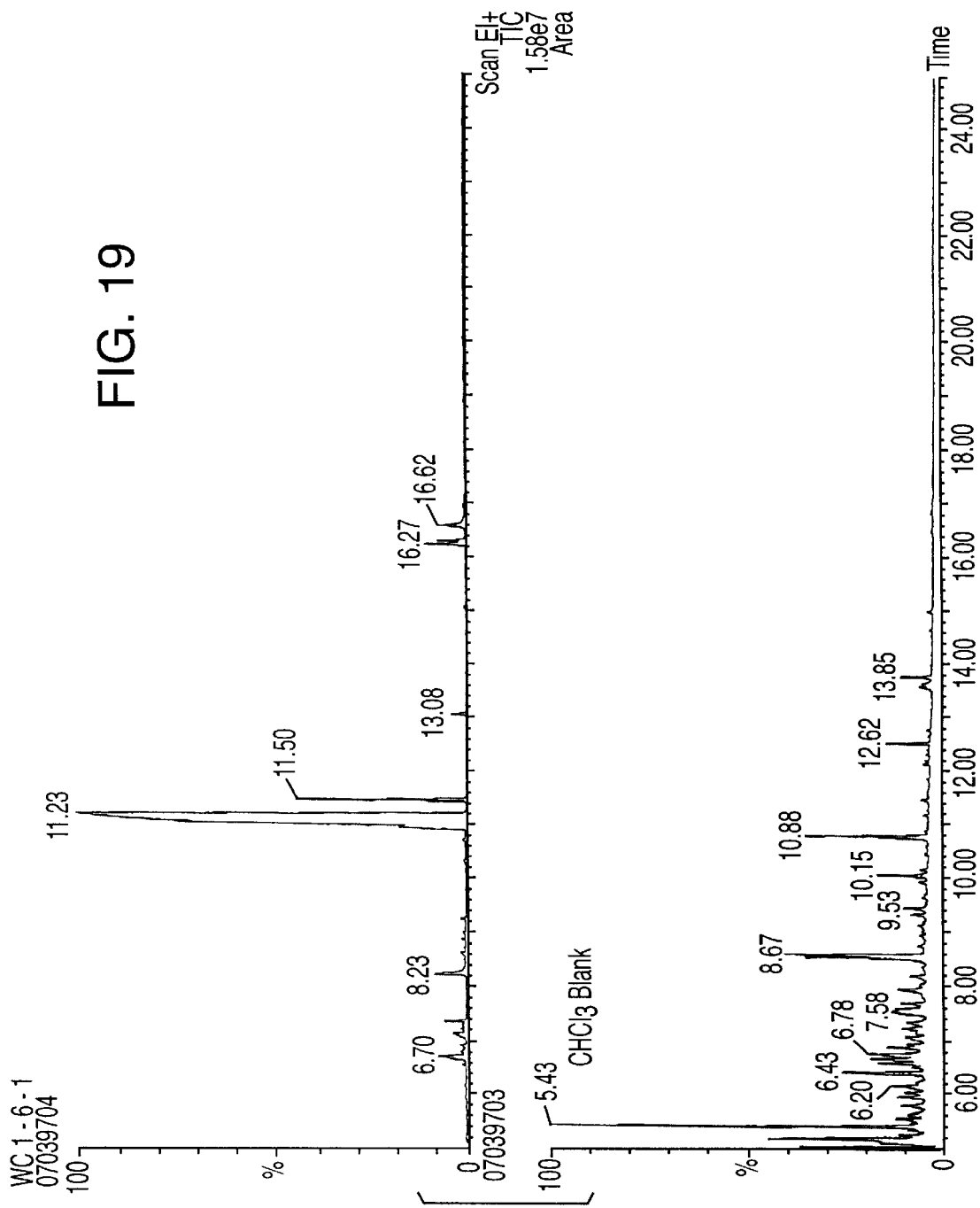
FIG. 19 is a NMR trace of fraction W-1-6 showing 4-cumylphenol.
Figure 20:
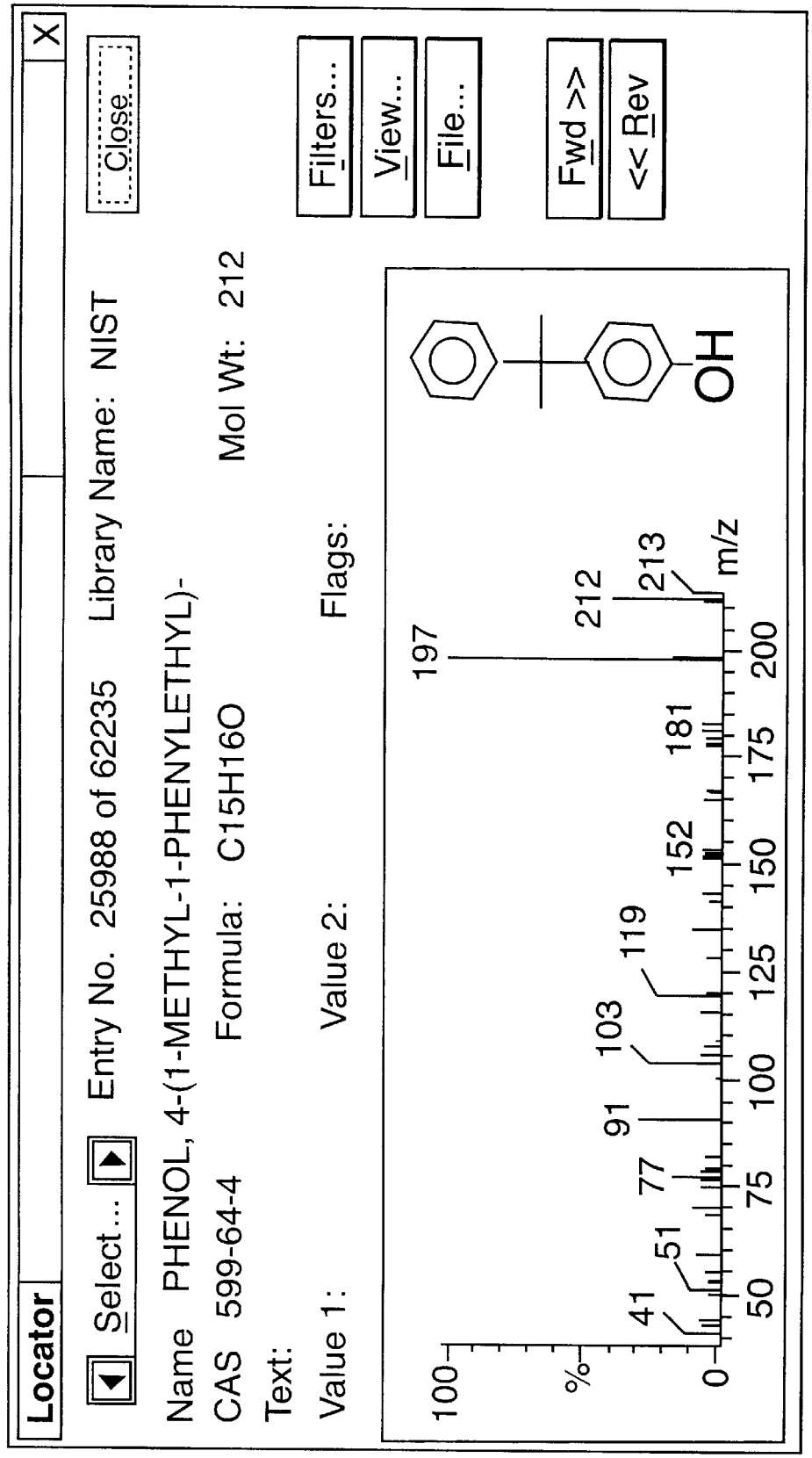
FIG. 20 is a mass spectrum, taken from the NIST Library, showing 4-cumylphenol.

The high COX II inhibitory activity of Wingstay fraction WC-1-6 suggested the presence of compounds with high inhibitory activity. Preparative thin layer chromatography of WC-1-5 gave three bands subsequently identified by mass spectral analysis and NMR to be 1) 2, 4-(dimethylbenzyl)-phenol (FIG. 18) and 2) 4-dimethylbenzyl-2,6-di-tert-butyl-phenol. GCMS analysis of WC-1-6 identified 4-dimethyl-benzylphenol, FIG. 19 and FIG. 20. Of the three compounds identified 4-cumylphenol (4-dimethyl-benzylphenol) (4-cumyl phenol) appeared to have the most promising chemistry. Sufficient quantities of pure 4-cumylphenol were purchased from a commercial source (Fisher Scientific).

The ability of pure 4-cumylphenol to inhibit the activity of COX II and possible inhibition of COX I was tested using biochemical assays as described in Example 2B. The results of these studies are shown in Table 8.

TABLE 8

Percent Inhibition of COX I, COX II, and 15-LO by 4-Cumylphenol

| Compound | Enzyme Assay | | |
| --- | --- | --- | --- |
| | Cox I | COX II | 15-LO |
| 1) 4-Cumylphenol | 1.6% | 22.4% | −40.0% |

EXAMPLE 9

Figure 21:
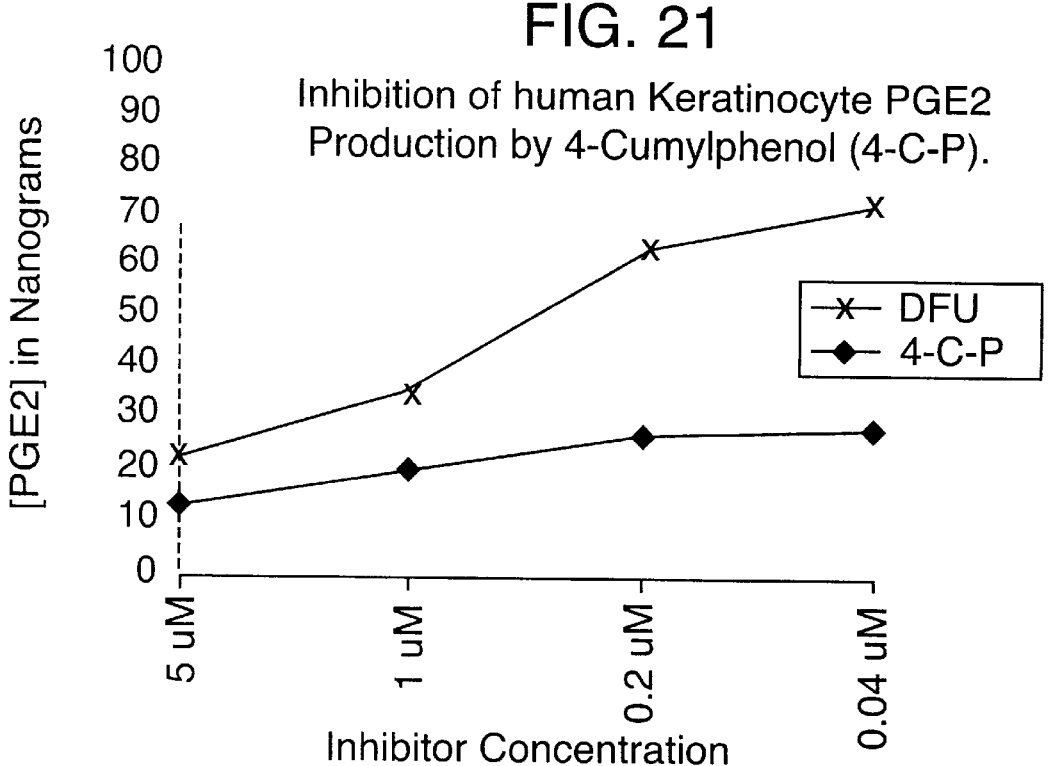
FIG. 21 graphically presents the results of an assay showing the inhibition of human keratinocyte $PGE_2$ production by 4-cumylphenol.

Assessment of the Biological Activity and Cytotoxicity of 4-Cumylphenol Using Cell-Based Assays 9A: Assessment of the Biological Activity of 4-Cumylphenol The ability of 4-cumylphenol to inhibit the enzymatic activity of COX II was tested using primary cultures of human foreskin keratinocytes. These cell studies were performed in an identical manner to the studies described in Example 6. Briefly, human keratinocytes were plated in 48-well plates (Nunc) and treated with high calcium medium to induce the upregulation of COX II (Leong, J., Hughes-Fulford, M., Rakhlin, A., Maclouf, J., and Goldyne, M., (1996), Exp. Cell Res., V224, p79). Twenty-four hours after treatment with high calcium media, duplicate wells were treated with 4-cumylphenol serially diluted in ethanol to produce final concentrations of 5, 1.0, 0.2, and 0.04 uM. Companion cultures were treated with an identical dilution series of the Merck COX II-specific inhibitor DFU. Twenty-four hours later, samples were removed from each treated well (as well as vehicle-treated control wells) and the amount of $PGE_2$ (a product of the COX II pathway) was quantified using a $PGE_2$-specific enzyme immunoassay (Cayman Chemical). ), as was done with the previously described COX I, COX II, and 15-LO biochemical assays (see Example 2B). The percent inhibition was calculated based on a comparison between vehicle treated control cultures and cultures treated with 4-cumylphenol or DFU. As shown in FIG. 21, 4-cumylphenol inhibited the production of $PGE_2$ by cultured human keratinocytes. Moreover, the degree of inhibition was dependent on the concentration of 4-cumylphenol added to the culture. Dose-dependent inhibition was also observed with the COX II-specific inhibitor DFU from Merck.

9B: Cytotoxicity of 4-Cumylphenol

To address the possibility that the inhibition of $PGE_2$ production by human keratinocytes treated with 4-cumylphenol was due to toxicity, a cell lactate dehydrogenase toxicity assay (Fisher Scientific) was performed. This assay was performed in an identical manner as that described in Example 6B. Briefly, lactate dehydrogenase (LDH; an intracellular enzyme) is released only in response to toxic stimuli and/or cell death. To do the assay, 48-well plates of cultured human keratinocytes were prepared and treated with the same concentrations of 4-cumylphenol as described above for the $PGE_2$ assay. One hour prior to harvesting culture media samples, duplicate wells were treated with a cell lysis buffer (Fisher Scientific) causing 100% cell death to occur. After culture media samples were collected from all wells, the amount of LDH present in each was determined using a colorometric assay (Fisher Scientific). The amount of LDH present in media samples taken from well treated with lysis buffer was assumed to be 100%. The amount of LDH released into the media of cultures treated with dehydroabietic acid methyl ester as well as vehicle-control media was determined using the colorometric assay and expressed as a percentage of that released by the 100% cell death wells.

Figure 22:
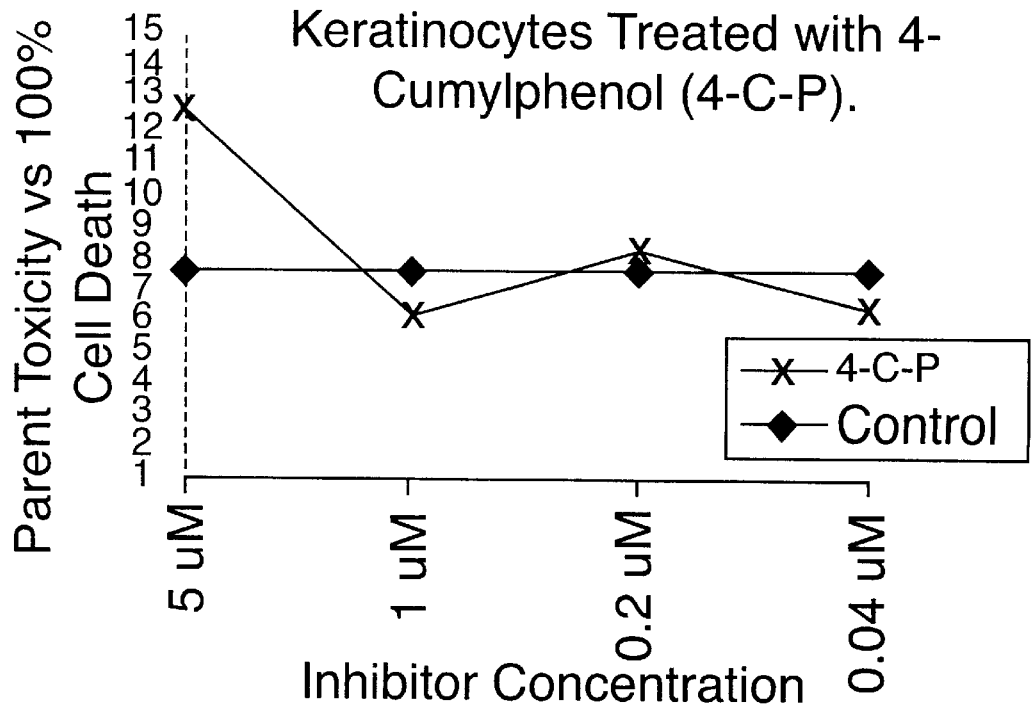
FIG. 22 graphically presents the results of an assay showing the lack of toxicity in cultures of human keratinocytes treated with 4-cumylphenol.

Vehicle treated control cultures exhibited percent toxicities ranging from 2 to 15% versus the 100% cell death control. No culture treated with 4-cumylphenol exhibited a percent toxicity greater than 12.7% versus the 100% cell death control (FIG. 22). As shown in FIG. 10, the percent toxicities determined for cultures treated with 4-cumylphenol were independent of the concentration of 4-cumylphenol used to treat the culture. The lack of appreciable toxicity in cultures treated with 4-cumylphenol is consistent with the lack of toxicity when treated cultures were examined microscopically.

EXAMPLE 10

Identification of 3-Methoxy-Aniline from Fractions Derived from Extract-6

10A: Identification of COX-II Inhibitory Fractions of Extract-6

Extract-6 (1.5 g) was initially fractionated by column chromatography on a 4.1×61 cm column with 80 g of silica gel (200–425 mesh, Aldrich). The column was equilibrated in $CH_2Cl_2$ and extract-6 was loaded in a minimum volume of $CH_2Cl_2$ (14 ml). The column was developed with a gradient of: A) $CH_2Cl_2$ (400 ml); B) $CH_2Cl_2$:MeOH 98:2 (v/v, 200 ml); C) $CH_2Cl_2$:MeOH 95:5 (v/v, 200 ml); D) $CH_2Cl_2$:MeOH 9:1 (v/v, 200 ml); E) $CH_2Cl_2$:MeOH 8:2 (v/v, 200 ml); F) $CH_2Cl_2$:MeOH 7:3 (v/v, 200 ml). Fractions with apparent similar composition as identified by analytical TLC were pooled as fractions 6-1 through 6-11) The pooled fractions had the following masses; fraction 6-1 (6 mg); 6-2

(54 mg); 6-3 (36 mg);6-4 (268 mg); 6-5 (169 mg); 6-6 (20 mg);6-7 (473 mg); 6-8 (5 mg); 6-8 (5 mg); 6-9 (102 mg); 6-10 (34 mg); 6-11 (68 mg). These X-6 fractions (X-6-1 to 6-11) were subsequently tested in the COX II biochemical assay in an identical manner as that described in Example 2. The results are presented in Table 9 below.

TABLE 9

Inhibition of Human Recombinant COX II by Fractions 6-1, -2, -3, -4, -5, -6, -7, -8, -9, -10, and -11.

| Fraction | Percent Inhibition of COX II |
| --- | --- |
| X-6-1 | 23.8% |
| X-6-2 | 19.7 |
| X-6-3 | 7.7 |
| X-6-4 | 19.9 |
| X-6-5 | 7 |
| X-6-6 | 9.85 |
| X-6-7 | 15 |
| X-6-8 | 11.9 |
| X-6-9 | 15.9 |
| X-6-10 | 10.6 |
| X-6-11 | 18.5 |

10B: Identification and Isolation of 3-Methoxy Aniline from a COX-II Inhibitory Fraction Derived from Extract-6

The potency of X-6-2 (19.7% inhibition of COX II) and the mass available (54 mg) warranted further fractionation. Methods used for chromatography of X-6-2 are described above in Example 10A. Fraction X-6-2 was further resolved into 10 fractions (X-6-1-1 to 10) by preparative TLC. Briefly, X-6-2 (XX mg) was loaded onto 1000 µm PK6F 60 µ silica gel preparative TLC plate (Whatman) and developed in hexane:ethyl acetate 3:1 (v/v). Bands were visualized at 254 nm and individually collected. The organic material was removed from the silica gel by stirring in the developing solvent mixture and then filtering. The mass recovered from each fraction was as follows X-6-2-1 (18 mg); 6-2-2 (3 mg); 6-2-3 (2 mg); 6-2-4 (5 mg); 6-2-5 (4 mg); 6-2-6 (6 mg); 6-2-7 (2 mg); 6-2-8 (2 mg); 6-2-9 (2 mg); 6-2-10 (1 mg). These sub-fractions were then tested for inhibitory activity using the COX II biochemical assay as described in Example 2. These results are presented below in Table 10.

TABLE 10

Inhibition of Huinan Recombinant COX II by Fractions 6-2-1, -2, -3, -4, -5, -6, -7, -8, -9, and -10.

| Fraction | Percent Inhibition of COX II |
| --- | --- |
| X-6-2-1 | 13.6% |
| X-6-2-2 | 16.11 |
| X-6-2-3 | 23.6 |
| X-6-2-4 | 14.2 |
| X-6-2-5 | 16.9 |
| X-6-2-6 | 0.55 |
| X-6-2-7 | 0.2 |
| X-6-2-8 | 12.2 |
| X-6-2-9 | 3 |
| X-6-2-10 | 6.11 |

10C: Identification of 3-Methoxy Aniline Based on GCMS and MS Data

Figure 23A:
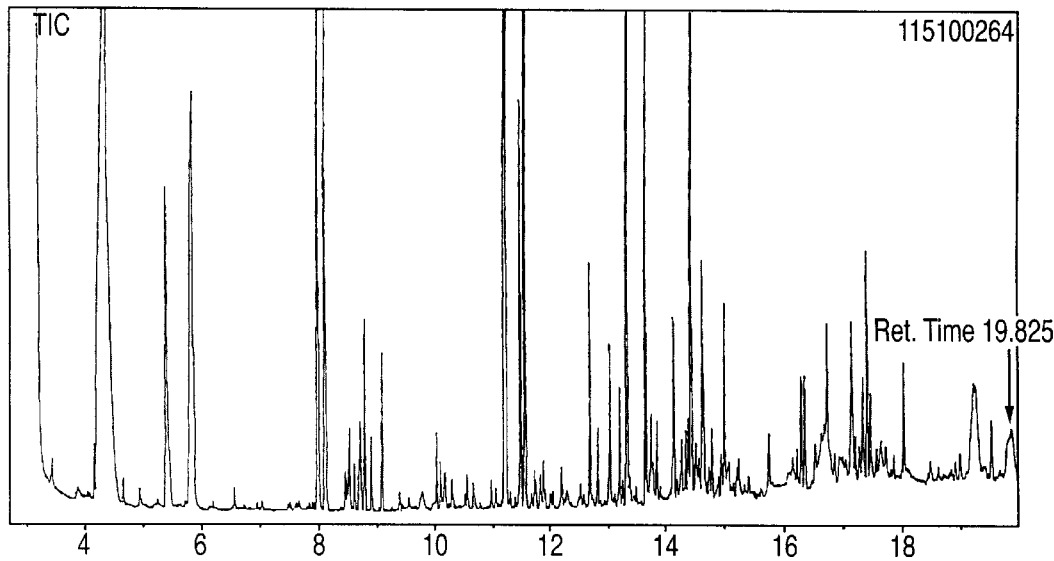
FIG. 23A is a chromatograph of fraction X-6-2-3 showing the 19.825 minute peak of 3-methoxy aniline (3-M-A).
Figure 23B:
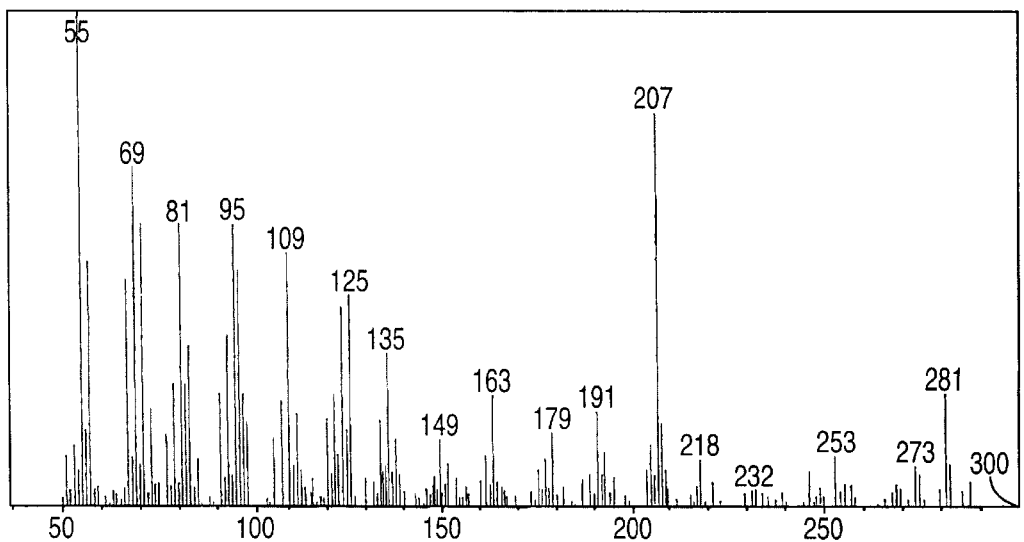
FIG. 23B is a mass spectrum showing 3-M-A.
Figure 23C:
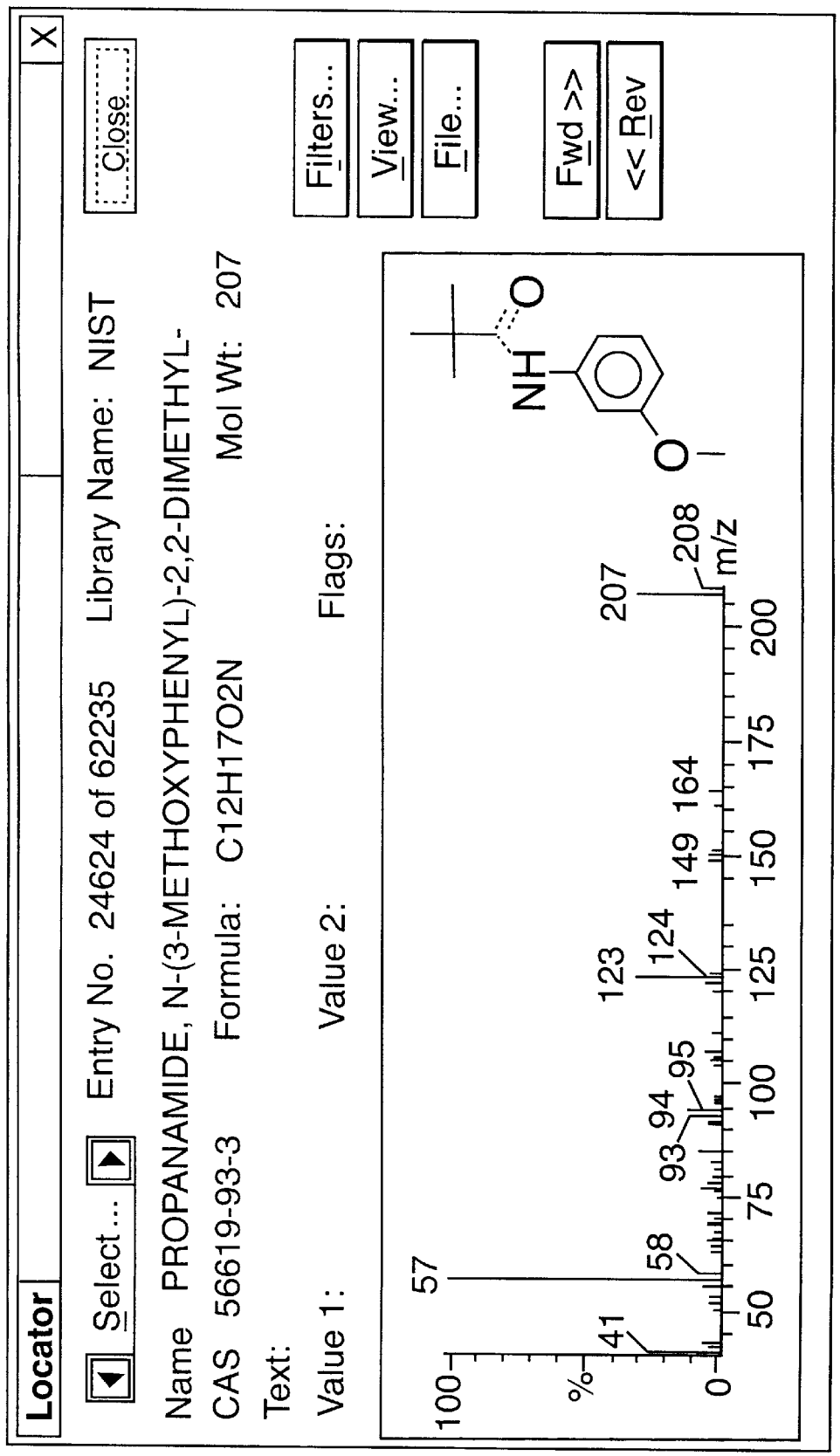
FIG. 23C is a mass spectrum of 3-M-A, taken from the NIST Library, that matches the mass spectrum of FIG. 23B.

Fraction X-6-2-3 had 23.6% inhibition in the biochemical COX II assay, warranting further studies to identify the compound responsible for the inhibitory activity. GC-MS was performed on X-6-2-3 with a Shimadzu QP5000 Mass Spectrometer in the Electron Impact Ionization mode coupled to a Hewlett Packard 5890 Gas Chromatograph. Fraction X-6-2-3 contained a peak at 19.825 minutes reten- tion time in the chromatograph (see FIG. 23A) that gave a mass spectrum (FIG. 23B) that matched with the mass spectrum of 3-methoxy aniline (propanamide, N-(3-methoxyphenyl)2,2-dimethyl) (FIG. 23C) from the NIST Library.

EXAMPLE 11

Figure 24:
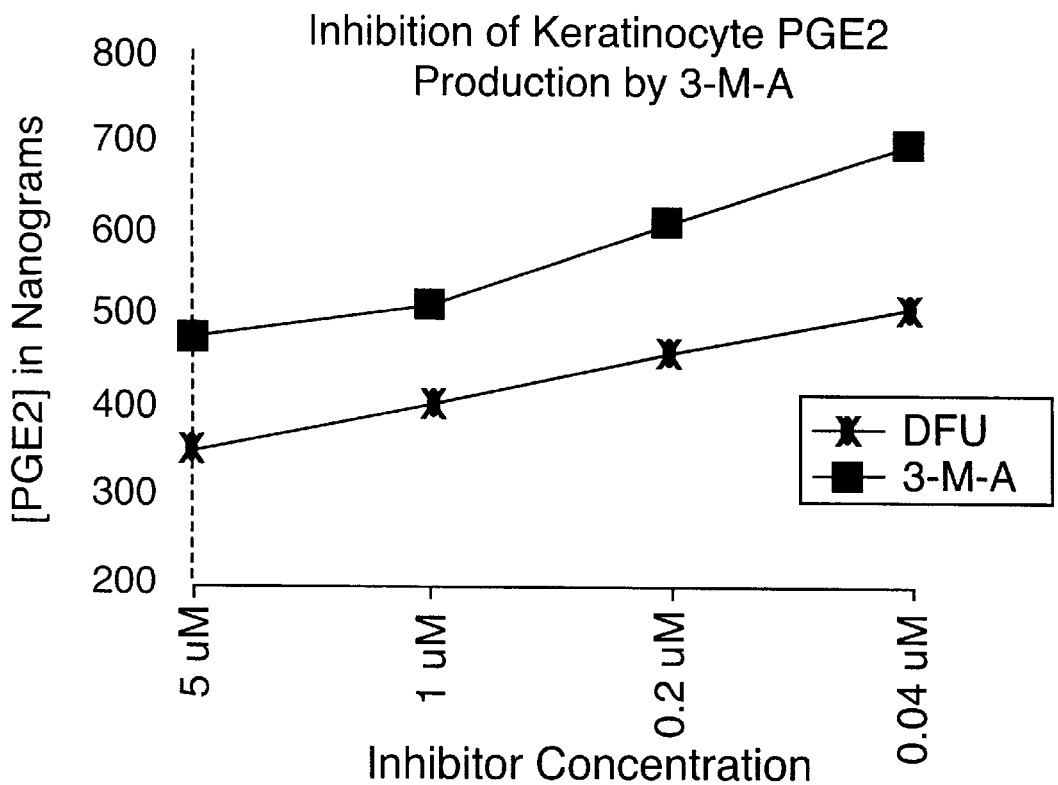
FIG. 24 graphically presents the results of an assay showing the inhibition of human keratinocyte $PGE_2$ production by 3-M-A.

Assessment of the Biological Activity and Cytotoxicity of 3-Methoxy-Aniline Using Cell-Based Assays 11A: Assessment of the Biological Activity of 3-Methoxy Aniline To evaluate the biological activities of 3-methoxy aniline, sufficient quantities of the compound were synthesized as detailed in Example 1C (above). The ability of 3-methoxy aniline (3-M-A) to inhibit the enzymatic activity of COX II was tested using primary cultures of human foreskin keratinocytes. These cell studies were performed in an identical manner to the studies described in Example 6. Briefly, human keratinocytes were plated in 48-well plates (Nunc) and treated with high calcium medium to induce the upregulation of COX II (Leong, J., Hughes-Fulford, M., Rakhlin, A., Maclouf, J., and Goldyne, M., (1996), Exp. Cell Res., V224, p79). Twenty-four hours after treatment with high calcium media, duplicate wells were treated with 3-M-A serially diluted in ethanol to produce final concentrations of 5, 1.0, 0.2, and 0.04 uM. Companion cultures were treated with an identical dilution series of the Merck COX II-specific inhibitor DFU. Twenty-four hours later, samples were removed from each treated well (as well as vehicle-treated control wells) and the amount of $PGE_2$ (a product of the COX II pathway) was quantified using a $PGE_2$-specific enzyme immunoassay (Cayman Chemical). ), As was done with the previously described COX I, COX II, and 15-LO biochemical assays (see Example 2B), the percent inhibition was calculated based on a comparison between vehicle treated control cultures and cultures treated with 3-M-A or DFU. As shown in FIG. 24, 3-M-A inhibited the production of $PGE_2$ by cultured human keratinocytes. Moreover, the degree of inhibition was dependent on the concentration of 3-M-A added to the culture. Dose-dependent inhibition was also observed with the COX II-specific inhibitor DFU from Merck.

11B: Cytotoxicity of 3-Methoxy Aniline

To address the possibility that the inhibition of $PGE_2$ production by human keratinocytes treated with 3-M-A was due to toxicity, a cell lactate dehydrogenase toxicity assay (Fisher Scientific) was performed. This assay was performed in an identical manner as that described in Example 6B. Briefly, lactate dehydrogenase (LDH; an intracellular enzyme) is released only in response to toxic stimuli and/or cell death. To do the assay, 48-well plates of cultured human keratinocytes were prepared and treated with the same concentrations of 3-M-A as described above for the $PGE_2$ assay. One hour prior to harvesting culture media samples, duplicate wells were treated with a cell lysis buffer (Fisher Scientific) causing 100% cell death to occur. After culture media samples were collected from all wells, the amount of LDH present in each was determined using a colorometric assay (Fisher Scientific). The amount of LDH present in media samples taken from well treated with lysis buffer was assumed to be 100%. The amount of LDH released into the media of cultures treated with 3-M-A as well as vehicle-control media was determined using the colorometric assay and expressed as a percentage of that released by the 100% cell death wells.

Figure 25:
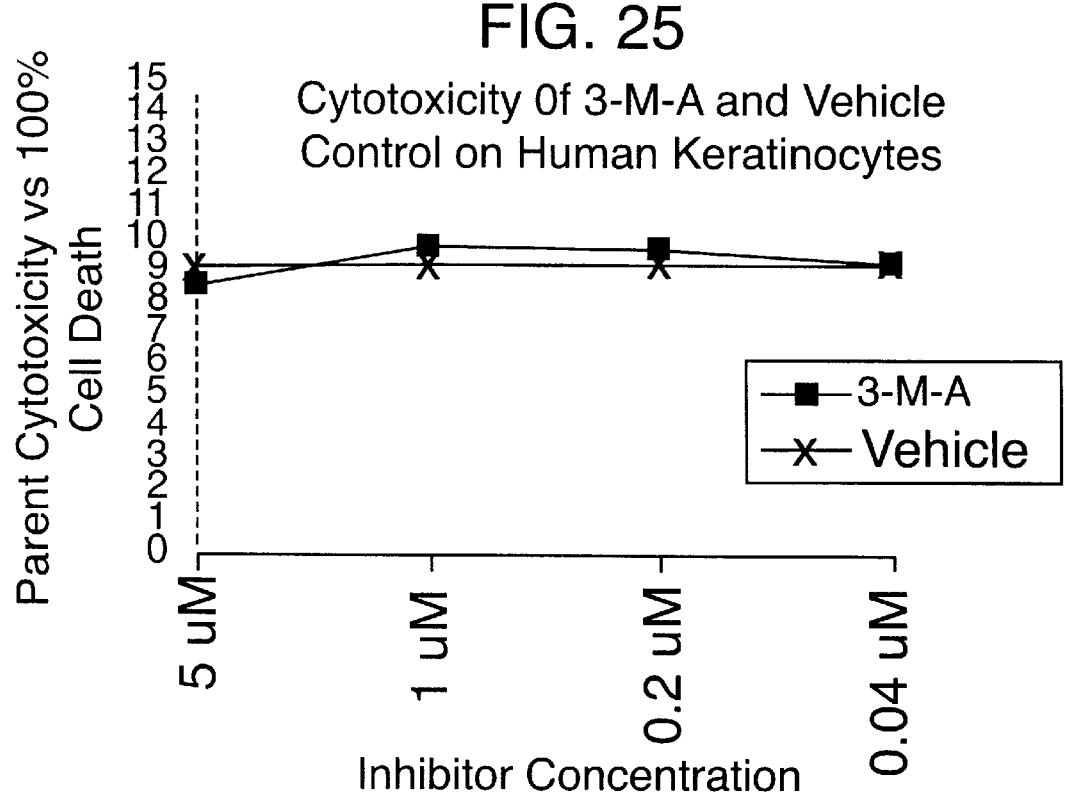
FIG. 25 graphically presents the results of an assay showing the lack of toxicity in cultures of human keratinocytes treated with 3-M-A.

Vehicle treated control cultures exhibited percent toxicities ranging from 2 to 15% versus the 100% cell death control. No culture treated with 3-M-A exhibited a percent toxicity greater than 10% versus the 100% cell death control (FIG. 25). As shown in FIG. 25, the percent toxicities determined for cultures treated with 3-M-A were independent of the concentration of 3-M-A used to treat the culture. The lack of appreciable toxicity in cultures treated with 3-M-A is consistent with the lack of toxicity when treated cultures were examined microscopically.

EXAMPLE 12
Administration of Compounds from Formula I for Inflammation Related Conditions Within this invention is a class of pharmaceutical compositions comprising of one or more compounds of Formula I and Formula II (or prodrugs of such compounds), in association with one or more non-toxic, pharmaceutically-acceptable carriers and/or diluents and/or adjuvants (referred to herein as "carrier" materials) and, if desired, other active ingredients. The compounds of the present invention may be administered by any suitable route, preferably in the form of pharmaceutical composition adapted to such a route, and in a dose effective for the treatment intended. For example, the composition may be administered intravascularly, intraperitoneally, subcutaneously, intramuscularly, or topically.

Oral or rectal dosage forms include capsules, tablets, pills, powders, cachets and suppositories. Liquid oral dosage forms include solutions and suspensions. Inhalation administration can be in the form of an oral of nasal spray, or by insufflation. The active ingredient may also be administered by injection as a composition where, for example, saline, dextrose, or water may be used as a suitable carrier.

The amount of therapeutically active compound that is administered and the dosage regimen for treating a disease condition with the compound and/or compositions of this invention depends on a variety of factors, including age, weight, sex and medical condition of the patient, the severity of the disease, the route and frequency of administration, and the particular compound employed. The pharmaceutical compositions may contain active ingredient in the range of about 0.1 to 2000 mg, most preferably between the range of about 1 and 100 mg. A daily dose of about 0.01 to 100 mg/kg body weight, preferably between 1 and 20 mg/kg body weight, may be appropriate. The daily dose can be administered in one to four doses per day.

In the case of psoriasis and other skin conditions, it may be preferable to apply a topical preparation of a compound of this invention to the affected area two to four times a day.

For inflammation of the eyes and other external tissues, e.g., mouth and skin, the formulations are preferably applied as a topical ointment or cream containing the active ingredients in a total amount of, for example, 0.075 to 30% w/w, preferably 0.4 to 15% w/w. When formulated in an ointment, the active ingredients may be employed with either paraffinic, a water miscible, or in a cream with an oil-in-water ointment base. If desired, the aqueous phase of the cream base may include, for example at least 30% w/w of a polyhydric alcohol such as propylene glycol, butane-1,3-diol, mannitol, sorbitol, glycerol, polyethylene glycol, and mixtures thereof. The topical formulation may include a compound that enhances absorption or penetration of the active ingredient through the skin or other affected areas, such as dimethylsulfoxide and related analogs. A transdermal device may also be used to administer the compounds of this invention or prodrug derivatives of this invention. Topical administration may be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. Preferably, a hydrophilic emulsifier is included together with a lipophilic emulsifier that acts as a stabilizer. It is also preferred to include both an oil and a fat. Together, the emulsifier(s) with or without stabilizer(s) make the so-called emulsifying wax, and the wax together with the oil and fat make the so-called emulsifying ointment base which forms the oily dispersed phase of the cream foundations. Emulsifiers and emulsion stabilizers suitable for use in the formulation of the present invention include Tween 60, Span 80, cetostearyl alcohol, myristyl alcohol, glyceryl monostearate, and sodium lauryl sulfate, among others.

Formulations suitable for topical administration to the eye also include eye drops wherein the active ingredients are dissolved or suspended in suitable carriers, especially an aqueous solvent for the active ingredients. The anti-inflammatory active ingredients are preferably present in concentrations of 0.5 to 20% w/w.

For therapeutic purposes, the compounds of this invention are ordinarily combined with one or more adjuvants appropriate to the indicated route of administration. The compounds may be mixed with lactose, sucrose, starch powder, cellulose esters of alkanioc acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then packaged as a tablet or capsule for convenient administration. Such tablets or capsules may contain controlled-release formulations such as dispersion of active agents in hydroxypropylmethyl cellulose. Formulations for parenteral administration may be in the form of aqueous or non-aqueous isotonic sterile injection solutions or suspensions. These solutions and suspensions may be prepared from sterile powder or granules having one or more of the carriers or diluents mentioned for the use of formulations for oral administration. The compounds may be dissolved in water, polyethylene glycol, propylene glycol, ethanol, corn oil, peanut oil, sesame oil, benzyl alcohol, sodium chloride, and/or various buffers. Other adjuvants and modes of administration are well and widely known in the pharmaceutical arts.

It will be obvious to those having skill in the art that many changes may be made to the details of the above-described embodiment of this invention without departing from the underlying principles thereof. The scope of the present invention should, therefore, be determined only by the following claims.

What is claimed is:

1. A method of treating an inflammatory disease responsive to treatment with a non-steroidal anti-inflammatory agent, comprising:
   administration to a patient in need of such treatment of a therapeutically effective amount of 4-cumylphenol or its salts or solvates thereof and a pharmaceutically acceptable carrier.

2. The method of claim 1 in which the anti-inflammatory agent selectively inhibits cyclooxygenase-II.

3. The method of claim 2 in which the anti-inflammatory agent selectively inhibits cyclooxygenase-II in preference to cyclooxygenase-I.

4. The method of claim 3 in which the degree of inhibition is dependent on the concentration of the 4-cumylphenol or its salt or solvate thereof.

5. The method of claim 1 in which the therapeutically effective amount comprises a daily dose of 0.01 to 100 mg/kg of patient body weight.

6. The method of claim 5 in which the therapeutically effective amount comprises a daily dose of 1 to 20 mg/kg of patient body weight.

7. The method of claim 1 in which the therapeutically effective amount comprises a 0.075 to 30% w/w of a topical or cream.

8. A method of treating cyclooxygenase mediated diseases advantageously treated by an active agent that selectively inhibits cyclooxygenase-II in preference to cyclooxygenase-I, comprising:

administering to a patient in need of such treatment a therapeutically effective amount of 4-cumylphenol or its salts or solvates thereof with or without a pharmaceutically acceptable carrier.

9. The method of claim 8 in which the degree of inhibition is dependent on the concentration of the 4-cumylphenol or its salt or solvate thereof.

10. The method of claim 8 in which the therapeutically effective amount comprises a daily dose of 0.01 to 100 mg/kg of patient body weight.

11. The method of claim 10 in which the therapeutically effective amount comprises a daily dose of 1 to 20 mg/kg of patient body weight.

12. The method of claim 8 in which the therapeutically effective amount comprises a 0.075 to 30% w/w of a topical or cream.

13. A method of treating inflammation in a patient for which non-steidal anti-inflammatory drugs may be contraindicated, comprising:

administration to a patient in need of such treatment of a therapeutically effective amount of 4-cumylphenol or its salts or solvates thereof and a pharmaceutically acceptable carrier.

14. The method of claim 13 in which the anti-inflammatory agent selectively inhibits cyclooxygenase-II.

15. The method of claim 13 in which the anti-inflammatory agent selectively inhibits cyclooxygenase-II in preference to cyclooxygenase-I.

16. The method of claim 15 in which the degree of inhibition is dependent on the concentration of the 4-cumylphenol or its salt or solvate thereof.

17. The method of claim 13 in which the therapeutically effective amount comprises a daily dose of 0.01 to 100 mg/kg of patient body weight.

18. The method of claim 17 in which the therapeutically effective amount comprises a daily dose of 1 to 20 mg/kg of patient body weight.

19. The method of claim 13 in which the therapeutically effective amount comprises a 0.075 to 30% w/w of a topical or cream.

* * * * *